US010316097B2

(12) United States Patent
Godard et al.

(10) Patent No.: US 10,316,097 B2
(45) Date of Patent: Jun. 11, 2019

(54) METHOD FOR THE TREATMENT OF EPILEPSY, EPILEPTOGENESIS, SEIZURES OR CONVULSIONS BY AN ANTI-COLONY-STIMULATING FACTOR 1 RECEPTOR (CSF-1R) ANTIBODY

(71) Applicant: UCB BIOPHARMA SPRL, Brussels (BE)

(72) Inventors: Patrice Marie Charles Godard, Brussels (BE); Rafal Marian Kaminski, Brussels (BE); Karine Josee Jeanne Leclercq, Brussels (BE); Jonathan Marie M Van Eyll, Brussels (BE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/577,035

(22) PCT Filed: May 25, 2016

(86) PCT No.: PCT/EP2016/061824
§ 371 (c)(1),
(2) Date: Nov. 27, 2017

(87) PCT Pub. No.: WO2016/189045
PCT Pub. Date: Dec. 1, 2016

(65) Prior Publication Data
US 2018/0142026 A1    May 24, 2018

(30) Foreign Application Priority Data
May 27, 2015   (EP) ..................... 15169367

(51) Int. Cl.
| | |
|---|---|
| *G01N 33/53* | (2006.01) |
| *A61K 39/395* | (2006.01) |
| *C07K 14/475* | (2006.01) |
| *C07K 14/48* | (2006.01) |
| *A61K 38/00* | (2006.01) |
| *A61K 38/18* | (2006.01) |
| *A61K 49/00* | (2006.01) |
| *A61K 49/16* | (2006.01) |
| *A61K 38/19* | (2006.01) |
| *A61K 38/20* | (2006.01) |
| *A61K 38/21* | (2006.01) |
| *A61K 38/17* | (2006.01) |
| *C07K 14/47* | (2006.01) |
| *C07K 16/28* | (2006.01) |
| *A61P 25/28* | (2006.01) |
| *A61P 25/18* | (2006.01) |
| *A61P 25/16* | (2006.01) |
| *A61K 39/00* | (2006.01) |

(52) U.S. Cl.
CPC .......... *C07K 16/2866* (2013.01); *A61P 25/16* (2018.01); *A61P 25/18* (2018.01); *A61P 25/28* (2018.01); *A61K 2039/505* (2013.01); *C07K 2317/20* (2013.01); *C07K 2317/70* (2013.01); *C07K 2317/76* (2013.01); *C07K 2317/92* (2013.01)

(58) Field of Classification Search
CPC ............ C07K 2317/76; C07K 2317/92; C07K 2317/24; C07K 2317/565; C07K 16/2803; C07K 2317/55; C07K 2317/56; C07K 16/2866; C07K 2317/70; A61K 39/39558; A61K 2039/505; A61K 2039/507; A61K 38/177; A61K 38/1774; G01N 2500/10; G01N 33/6869; A61P 25/00; A61P 25/16; A61P 25/18; A61P 25/28
See application file for complete search history.

(56) References Cited

U.S. PATENT DOCUMENTS

| | | | | |
|---|---|---|---|---|
| 8,080,246 | B2 * | 12/2011 | Lin ..................... | C07K 14/7153 424/134.1 |
| 8,206,715 | B2 * | 6/2012 | Wong ................. | C07K 16/2866 424/143.1 |
| 8,470,977 | B2 * | 6/2013 | Haegel ............... | C07K 16/2866 530/387.1 |
| 9,161,968 | B2 * | 10/2015 | Wyss-Coray ........ | A61K 38/193 |
| 9,605,070 | B2 * | 3/2017 | Sabatos-Peyton ......................... A61K 39/3955 |
| 9,770,486 | B2 * | 9/2017 | Luo ...................... | A61K 38/193 |
| 9,884,913 | B2 * | 2/2018 | Sabatos-Peyton ......................... A61K 39/3955 |
| 2009/0317403 | A1 * | 12/2009 | Aharinejad ........ | C12N 15/1136 424/158.1 |
| 2010/0136007 | A1 * | 6/2010 | Lin ..................... | C07K 14/7153 424/134.1 |
| 2011/0274683 | A1 * | 11/2011 | Wong ................. | C07K 16/2866 424/130.1 |

(Continued)

FOREIGN PATENT DOCUMENTS

| | | | | |
|---|---|---|---|---|
| WO | WO2004/044159 | | * 5/2004 | |
| WO | WO-2009112245 A1 | * 9/2009 | ......... C07K 16/2866 |

(Continued)

OTHER PUBLICATIONS

Blight Nat. Neurosci. 2002. 5: 1051-4.*

(Continued)

*Primary Examiner* — Chang-Yu Wang
(74) *Attorney, Agent, or Firm* — Saliwanchik, Lloyd & Eisenschenk

(57) ABSTRACT

The present invention pertain an inhibitor of CSF-1R activity for use in the treatment and/or prophylaxis of neurologic diseases and new method of treatment of neurologic diseases.

8 Claims, 7 Drawing Sheets

Specification includes a Sequence Listing.

(56) References Cited

U.S. PATENT DOCUMENTS

| | | | | |
|---|---|---|---|---|
| 2015/0119267 | A1* | 4/2015 | Joyce | C12Q 1/6886 506/9 |
| 2015/0218274 | A1* | 8/2015 | Sabatos-Peyton | A61K 39/3955 424/136.1 |
| 2016/0200821 | A1* | 7/2016 | Craggs | C07K 16/2866 424/172.1 |
| 2017/0190777 | A1* | 7/2017 | Sabatos-Peyton | A61K 39/3955 |
| 2017/0198041 | A1* | 7/2017 | Sabatos-Peyton | A61K 39/3955 |
| 2017/0342148 | A1* | 11/2017 | Heymann | C07K 16/244 |
| 2018/0094067 | A1* | 4/2018 | Wong | C07K 16/2818 |
| 2018/0222974 | A1* | 8/2018 | Easley-Neal | A61K 39/3955 |

FOREIGN PATENT DOCUMENTS

| | | |
|---|---|---|
| WO | WO 2013/119716 | 8/2013 |
| WO | WO 2015/028455 | 3/2015 |

OTHER PUBLICATIONS

Schmidt et al. Annu. Rev. Biomed. Eng. 2003. 5: 293-347.*
Hoke et al. Nat. Clin. Pract. Neurol. 2006: 448-454.*
Anger. Neurotoxicology 1991. 12: 403-13.*
Tayebati. Mech. Ageing Dev. 2006. 127: 100-8.*
Sarter. Neurosci. and Biobehav. Rev. 2004. 28: 645-650.*
The factsheet of multiple sclerosis retrieved from the NINDS website: www.ninds.nih.gov/Disorders/All-Disorders/Multiple-Sclerosis-Information-Page on Sep. 13, 2018.*
T Hart et al. Curr. Opin. Neurol. 2003. 16: 375-383.*
Chang et al. N. Engl. J. Med. 2003; 349:1257-66.*
Dagher, N. N. et al. "Colony-stimulating factor 1 receptor inhibition prevents microglial plaque association and improves cognition in 3xTg-AD mice" *Journal of Neuroinflammation*, Aug. 1, 2015, pp. 1-14, vol. 12, No. 139.
Elmore, M. R. P. et al. "CSF1 receptor signaling is necessary for microglia viability, which unmasks a cell that rapidly repopulates the microglia-depleted adult brain" *Neuron*, Apr. 16, 2014, pp. 1-30, vol. 82, No. 2.
Hume, D. A. et al. "Therapeutic applications of macrophage colony-stimulating factor-1 (CSF-1) and antagonists of CSF-1 receptor (CSF-1R) signaling" *Blood*, Feb. 23, 2012, pp. 1810-1820, vol. 119, No. 8.
Olmos-Alonso, A. et al. "Pharmacological targeting of CSFIR inhibits microglial proliferation and prevents the progression of Alzheimer's-like pathology" *Brain*, Jan. 8, 2016, pp. 891-907, vol. 139, No. 3.
Rice, R. A. et al. "Elimination of Microglia Improves Functional Outcomes Following Extensive Neuronal Loss in the Hippocampus" *The Journal of Neuroscience*, Jul. 8, 2015, pp. 9977-9989, vol. 35, No. 27.
Written Opinion in International Application No. PCT/EP2016/061824, dated Aug. 2, 2016, pp. 1-8.

* cited by examiner

SEQUENCE LISTING

```
<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: CA019_969 Ab sequences CDR-L1
<220> FEATURE:
<221> NAME/KEY: CDR-L1
<222> LOCATION: (1)..(11)

<400> SEQUENCE: 1

Leu Ala Ser Glu Asp Ile Tyr Asp Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CA019_969 Ab sequences CDRL2
<220> FEATURE:
<221> NAME/KEY: CDR-L2
<222> LOCATION: (1)..(7)

<400> SEQUENCE: 2

Tyr Ala Ser Ser Leu Gln Asp
1               5

<210> SEQ ID NO 3
<211> LENGTH: 9
<212> TYPE: PRT
<213> ORGANISM: Artificial Sequence
<220> FEATURE:
<223> OTHER INFORMATION: CA019_969 Ab sequences CDR-L3
```

```
<220> FEATURE:
<221> NAME/KEY: CDR-L3
<222> LOCATION: (1)..(9)

<400> SEQUENCE: 3

Leu Gln Asp Ser Glu Tyr Pro Trp Thr
1               5

<210> SEQ ID NO 4
<211> LENGTH: 12
<212> TYPE: PRT
<213> ORGANISM: Artificial Sequence
<220> FEATURE:
<223> OTHER INFORMATION: CA019_969 Ab sequences CDR-H1
<220> FEATURE:
<221> NAME/KEY: CDR-H1
<222> LOCATION: (1)..(12)

<400> SEQUENCE: 4

Gly Phe Ser Leu Thr Thr Tyr Gly Met Gly Val Gly
1               5                   10

<210> SEQ ID NO 5
<211> LENGTH: 16
<212> TYPE: PRT
<213> ORGANISM: Artificial Sequence
<220> FEATURE:
<223> OTHER INFORMATION: CA019_969 Ab sequences CDR-H2
<220> FEATURE:
<221> NAME/KEY: CDR-H2
<222> LOCATION: (1)..(16)

<400> SEQUENCE: 5

Asn Ile Trp Trp Asp Asp Lys Tyr Tyr Asn Pro Ser Leu Lys Asn
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: CA019_969 Ab sequences CDR-H3
<220> FEATURE:
<221> NAME/KEY: CDR-H3
<222> LOCATION: (1)..(16)

<400> SEQUENCE: 6

Ile Gly Pro Ile Lys Tyr Pro Thr Ala Pro Tyr Arg Tyr Phe Asp Phe
1               5                   10                  15

<210> SEQ ID NO 7
<211> LENGTH: 107
<212> TYPE: PRT
<213> ORGANISM: Artificial Sequence
<220> FEATURE:
<223> OTHER INFORMATION: 969 gL7 V-region
<220> FEATURE:
<221> NAME/KEY: 969 gL7 V-region
<222> LOCATION: (1)..(107)

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
                20                  25                  30

Leu Ala Trp Tyr Gln Gln Lys Pro Gly Lys Ala Pro Lys Leu Leu Ile
            35                  40                  45
```

Tyr Tyr Ala Ser Ser Leu Gln Asp Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln Asp Ser Glu Tyr Pro Trp
                 85                  90                  95

Thr Phe Gly Gly Gly Thr Lys Val Glu Ile Lys
                100                 105

<210> SEQ ID NO 8
<211> LENGTH: 321
<212> TYPE: DNA
<213> ORGANISM: Artificial Sequence
<220> FEATURE:
<223> OTHER INFORMATION: 969 gL7 V-region
<220> FEATURE:
<221> NAME/KEY: 969 gL7 V-region
<222> LOCATION: (1)..(321)

<400> SEQUENCE: 8
gacatacaga tgactcagtc accctcaagc ctgagtgcca gtgtgggaga cagggtgaca      60
atcacctgtc tggcctccga ggatatctac gataacctgg catggtatca gcagaaacct    120
ggaaaggctc ccaagctcct gatttattat gcctcctctc tccaagacgg cgttccatct    180
cggttcagcg gaagcggctc cgggacggat tacacactga caattagctc tctgcaaccg    240
gaggattttg ctacttacta ctgcctgcaa gactccgaat accatggac cttcggtggt     300 ggcaccaaag tggaaatcaa g                                              321

<210> SEQ ID NO 9
<211> LENGTH: 125
<212> TYPE: PRT
<213> ORGANISM: Artificial Sequence
<220> FEATURE:
<223> OTHER INFORMATION: 969 gH2 V-region
<220> FEATURE:
<221> NAME/KEY: 969 gH2 V-region
<222> LOCATION: (1)..(125)

<400> SEQUENCE: 9

Glu Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Thr Thr Tyr
                 20                  25                  30

Gly Met Gly Val Gly Trp Ile Arg Gln Pro Pro Gly Lys Ala Leu Glu
             35                  40                  45

Trp Leu Ala Asn Ile Trp Trp Asp Asp Asp Lys Tyr Tyr Asn Pro Ser
 50                  55                  60

Leu Lys Asn Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Gly Pro Ile Lys Tyr Pro Thr Ala Pro Tyr Arg Tyr
                100                 105                 110

Phe Asp Phe Trp Gly Gln Gly Thr Met Val Thr Val Ser
            115                 120                 125

<210> SEQ ID NO 10
<211> LENGTH: 375
<212> TYPE: DNA
<213> ORGANISM: Artificial Sequence
<220> FEATURE:
<223> OTHER INFORMATION: 969 gH2 V-region
<220> FEATURE:
<221> NAME/KEY: 969 gH2 V-region
<222> LOCATION: (1)..(375)

<400> SEQUENCE: 10

```
gaagtgacac tcaaggagtc tggacccgct ctggtgaaac caacccaaac actcactttg      60
acatgtactt ttagtggctt ctcattgact acctatggaa tgggcgtggg atggatcaga     120
cagccacctg gcaaggctct ggaatggctg gccaacatct ggtgggatga cgacaagtac     180
tataacccgt ccctgaaaaa ccggctgacc attagcaagg atacttctaa aaatcaagtg     240
gtgctgacca tgacaaatat ggatcccgtt gacaccgcaa cctactactg cgcccgcatt     300
ggtcccataa agtaccctac ggcaccttac cgatatttcg actttggggg ccaagggaca     360
atggttactg tctcg                                                      375
```

<210> SEQ ID NO 11
<211> LENGTH: 972
<212> TYPE: PRT
<213> ORGANISM: Artificial Sequence
<220> FEATURE:
<223> OTHER INFORMATION: Amino acid sequence for CSF-1R

<400> SEQUENCE: 11

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
        130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255
```

```
Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
    515                 520                 525

Leu Leu Leu Leu Leu Leu Leu Leu Tyr Lys Tyr Lys Gln Lys Pro
530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
            565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670
```

```
Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
            725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
            805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
            850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
            885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970

<210> SEQ ID NO 12
<211> LENGTH: 277
<212> TYPE: PRT
<213> ORGANISM: Artificial Sequence
<220> FEATURE:
<223> OTHER INFORMATION: Amino acid sequence for CSF-1R

<400> SEQUENCE: 12

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
50                  55                  60
```

-continued

```
Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val
        275

<210> SEQ ID NO 13
<211> LENGTH: 49
<212> TYPE: PRT
<213> ORGANISM: Artificial Sequence
<220> FEATURE:
<223> OTHER INFORMATION: Amino acid sequence for CSF-1R

<400> SEQUENCE: 13

Met Arg His Thr Asn Tyr Ser Phe Ser Pro Trp His Gly Phe Thr Ile
  1               5                  10                  15

His Arg Ala Lys Phe Ile Gln Ser Gln Asp Tyr Gln Cys Ser Ala Leu
                 20                  25                  30

Met Gly Gly Arg Lys Val Met Ser Ile Ser Ile Arg Leu Lys Val Gln
             35                  40                  45

Lys

<210> SEQ ID NO 14
<211> LENGTH: 493
<212> TYPE: PRT
<213> ORGANISM: Artificial Sequence
<220> FEATURE:
<223> OTHER INFORMATION: Amino acid sequence for CSF-1R (SNP V32G,
      A245S, H247P, V279M, position underlined)

<400> SEQUENCE: 14

Ile Pro Val Ile Glu Pro Ser Val Pro Glu Leu Val Val Lys Pro Gly
  1               5                  10                  15

Ala Thr Val Thr Leu Arg Cys Val Gly Asn Gly Ser Val Glu Trp Asp
                 20                  25                  30
```

```
Gly Pro Pro Ser Pro His Trp Thr Leu Tyr Ser Asp Gly Ser Ser
             35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
             100                 105                 110

Pro Val Leu Glu Ala Gly Val Ser Leu Val Arg Val Arg Gly Arg Pro
         115                 120                 125

Leu Met Arg His Thr Asn Tyr Ser Phe Ser Pro Trp His Gly Phe Thr
     130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Arg Leu Lys Val
                 165                 170                 175

Gln Lys Val Ile Pro Gly Pro Ala Leu Thr Leu Val Pro Ala Glu
             180                 185                 190

Leu Val Arg Ile Arg Gly Glu Ala Ala Gln Ile Val Cys Ser Ala Ser
         195                 200                 205

Ser Val Asp Val Asn Phe Asp Val Phe Leu Gln His Asn Asn Thr Lys
     210                 215                 220

Leu Ala Ile His Gln Gln Ser Asp Phe His Asn Arg Tyr Gln Lys
225                 230                 235                 240

Val Leu Thr Leu Asn Leu Asp Gln Val Asp Phe Gln His Ala Gly Asn
                 245                 250                 255

Tyr Ser Cys Val Ala Ser Asn Val Gln Gly Lys His Ser Thr Ser Met
             260                 265                 270

Phe Phe Arg Val Val Glu Ser Ala Tyr Leu Asn Leu Ser Ser Glu Gln
         275                 280                 285

Asn Leu Ile Gln Glu Val Thr Val Gly Glu Gly Leu Asn Leu Lys Val
     290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                 325                 330                 335

Thr Lys Asp Thr Tyr Arg His Thr Phe Thr Leu Ser Leu Pro Arg Leu
             340                 345                 350

Lys Pro Ser Glu Ala Gly Arg Tyr Ser Phe Leu Ala Arg Asn Pro Gly
         355                 360                 365

Gly Trp Arg Ala Leu Thr Phe Glu Leu Thr Leu Arg Tyr Pro Pro Glu
     370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                 405                 410                 415

Gly His Thr Asp Arg Cys Asp Glu Ala Gln Val Leu Gln Val Trp Asp
             420                 425                 430

Asp Pro Tyr Pro Glu Val Leu Ser Gln Glu Pro Phe His Lys Val Thr
         435                 440                 445
```

```
Val Gln Ser Leu Leu Thr Val Glu Thr Leu Glu His Asn Gln Thr Tyr
            450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
                485                 490

<210> SEQ ID NO 15
<211> LENGTH: 512
<212> TYPE: PRT
<213> ORGANISM: Artificial Sequence
<220> FEATURE:
<223> OTHER INFORMATION: sequence of human CSF-1R extracellular domain

<400> SEQUENCE: 15

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320
```

-continued

```
Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
        340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
            405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
            485                 490                 495

Ala Phe Ile Pro Ile Ser Ala Gly Ala His Thr His Pro Pro Asp Glu
            500                 505                 510
```

METHOD FOR THE TREATMENT OF EPILEPSY, EPILEPTOGENESIS, SEIZURES OR CONVULSIONS BY AN ANTI-COLONY-STIMULATING FACTOR 1 RECEPTOR (CSF-1R) ANTIBODY

CROSS-REFERENCE TO RELATED APPLICATION

This application is the U.S. national stage application of International Patent Application No. PCT/EP2016/061824, filed May 25, 2016.

The Sequence Listing for this application is labeled "Seq-List.txt" which was created on Jun. 1, 2016 and is 26 KB. The entire content of the sequence listing is incorporated herein by reference in its entirety.

The present invention relates generally to methods of treating neurological disease and more specifically to an anti-CSF-1R antibody for the treatment of neurological diseases.

There exist a wide variety of neurological diseases associated with neuroinflammatory responses, with most prominent being for example Alzheimer's disease, Amyotrophic lateral sclerosis (ALS), Autism, Creutzfeldt-Jacob disease, Meningitis, Multiple Sclerosis, Parkinson's disease, stroke, traumatic brain injury or epilepsy, epileptogenesis and seizure disorders and convulsion in general.

The World Health Organisation (WHO) and the International League Against Epilepsy (ILAE) define epilepsy as a chronic, recurrent, repetitive neurological disorder consisting of paroxysmal phenomena caused by excessive and chaotic discharges in neuronal brain cells. Its incidence has two peaks: one in childhood and adolescence and a second more marked one over the age of 60. According to the International Bureau for Epilepsy (IBE), some 50 million people suffer from epilepsy worldwide, with 20-30% of them suffering more than one seizure per month (Forsgren et al., Eur J Neurol 2005; 12:245-53).

The number of new epilepsy cases per year worldwide ranges between 24 and 53 cases per 100,000 inhabitants. In Europe, from the prevalence studies carried out in different countries and years, it was calculated that 0.9 million children and adolescents, 1.9 million adults of an age between 20 and 64 years, and 0.6 million older person of 65+ years are afflicted by epilepsy (Forsgren et al., Eur J Neurol 2005; 12:245-53).

Epilepsy is considered to comprise a diverse set of chronic neurological disorders characterized by seizures. These seizures may be recurrent and unprovoked, or may constitute single seizures combined with brain alterations increasing the chance of future seizures. Epileptic seizures typically result from abnormal, excessive or hypersynchronous neuronal activity in the brain.

Epilepsy is one of the most common neurological diseases with a prevalence of approximately 1% in global populations. According the most recent definition provided by the International League Against Epilepsy "an epileptic seizure is a transient occurrence of signs and/or symptoms due to abnormal excessive or synchronous neuronal activity in the brain" and "epilepsy is a disorder of the brain characterized by an enduring predisposition to generate epileptic seizures, and by the neurobiologic, cognitive, psychological, and social consequences of this condition." (Fisher et al., 2014).

The knowledge about epilepsy causes evolves rapidly since the advent of whole genome sequencing technologies and growing understanding of human genome. In addition, novel concepts and technologies in molecular cell biology and genetics have revolutionized our understanding of epilepsy pathophysiology. Neuroimaging techniques are now allowing an unprecedented understanding of the brain circuits and structures involve in seizure generation and epilepsy progression. Finally, in neurophysiologic techniques, such as electroencephalography (EEG) or in vitro electrophysiology provide further information about the role of neuronal networks in epilepsy.

There exist different types of seizures and epilepsy etiology, e.g. generalized seizures, focal seizures and seizures of unknown origin. Focal seizures are conceptualized as originating at some point within networks limited to one hemisphere (involving a specific area of the cerebral cortex), while generalized seizures are conceptualized as originating at some point within and rapidly engaging bilaterally distributed networks (involving the entire cerebral cortex) (Berg and Scheffer, 2011). Current classification of seizures by the International League Against Epilepsy (ILAE) published by Berg et al., 2010 comprise a) generalized seizures, which means in particular tonic-clonic (in any combination), absence (typical, atypical, absence with special features, myoclonic absence, eyelid myoclonia), myoclonic (myoclonic, myoclonic atonic, myoclonic tonic, clonic, tonic, atonic), b) focal seizures with and without impairment of consciousness or awareness and c) seizures of unknown origin (epileptic spasms).

Focal seizures without impairment of consciousness or awareness are i) with observable motor or autonomic components. This roughly corresponds to the concept of "simple partial seizure", whereby "focal motor" and "autonomic" are terms that may adequately convey this concept depending on the seizure manifestations. Or ii) correspond to involving subjective sensory or psychic phenomena only. This corresponds to the concept of an "aura".

Focal seizures with impairment of consciousness or awareness roughly correspond to the concept of complex partial seizure" with evolving to a bilateral, convulsive seizure (involving tonic, clonic, or tonic and clonic components). This expression replaces the term "secondarily generalized seizure."

Also, the main etiologic factors have nowadays been better defined: 1) genetic causes: a direct result of a known or presumed genetic defect(s) in which seizures are the core symptom of the disorder; 2) structural/metabolic causes: a distinct structural or metabolic condition or disease that has been demonstrated to be associated with a substantially increased risk of developing epilepsy; 3) unknown causes, when the nature of the underlying cause cannot be determined (Berg and Scheffer, 2011).

Furthermore, novel concepts about processes leading to epilepsy, i.e. epileptogenesis, are now being introduced and drive further research efforts in this filed. Epileptogenesis refers to the development and extension of tissue capable of generating spontaneous seizures, resulting in (1) development of an epileptic condition and/or (2) progression after the condition is established (Pitkänen et al., (2013). Disease or syndrome modification has two components: antiepileptogenesis and comorbidity modification.

Antiepileptogenesis is a process that counteracts the effects of epileptogenesis, including prevention, seizure modification, and cure. Regarding prevention, complete prevention aborts the development of epilepsy. Partial prevention can delay the development of epilepsy or reduce its severity. For example, seizures occur but they may be fewer in frequency, shorter, or of milder seizure type (seizure modification). Antiepileptogenesis can also prevent or reduce the progression of epilepsy after it has already been established.

Comorbidity Modification is meant as the treatment that alleviates or reverses the symptomatic development or progression of epilepsy-related comorbidities, such as anxiety, depression, somato-motor impairment, or cognitive decline.

A curative treatment is defined as a complete and permanent reversal of epilepsy, such that no seizures occur after treatment withdrawal (Pitkänen et al., 2013).

Novel therapeutic approaches aiming at disease modification in epilepsy are being proposed when the disease-modifying agent can be given prior to or after epilepsy onset. If such treatment is given prior to epilepsy onset, it could prevent or delay the development of epilepsy. When such a treatment is given after the diagnosis of epilepsy, it could alleviate seizure severity, prevent or reduce the progression of epilepsy, or change the seizures from drug resistant to drug sensitive.

The above described therapeutic concepts are fundamentally different from the current standard of care in epilepsy, which includes antiepileptic drugs (AEDs) targeting neuronal excitability mechanisms and thereby providing only anti-seizure effects. These drugs do not address the underlying causes or pathophysiology of epilepsy and 30-40% of patients with epilepsy suffer from uncontrolled seizures and comorbidities associated with the disease, despite an impressive armamentarium of more than 20 AEDs available on the market.

This creates an important unmet medical need to provide more efficacious drugs with neurologic disease modifying properties.

It is appreciated that inflammation has an indicative role in the pathophysiology of human epilepsy and epileptogenesis. In particular, microglial cells activation is associated with an induction of major pro-inflammatory pathways observed in human temporal lobe epilepsy (TLE), experimental models of TLE and epileptogenesis. This is mainly suggested by a range of studies performed on brain tissues obtained from both patients and rodent models with TLE, which indicate strong up-regulation of genes associated with the immune/inflammatory pathways, including several chemokines and pro-inflammatory cytokines. It is hypothesized that chronically activated microglial cells release pro-inflammatory cytokines (e.g. TNFa, IL1b), which then act to increase neuronal excitability and trigger seizures. This is best documented for IL1b, which is able to exacerbate seizure activity in experimental models, while gene knock-down or inhibition of IL1b production has anticonvulsant effects and may modify the course of the disease in experimental models.

However currently available validated drug targets controlling microglia activity are rather sparse and existing therapeutic approaches mainly focus on new chemical entities (NCEs). For example Elmore et al., 2014, published work where a small molecule compound (PLX3397) was used to inhibit the colony-stimulating factor 1 receptor (CSF-1R) provided data confirming that this receptor is a key regulator of microglia function and viability.

The colony-stimulating factor 1 (CSF-1) and the structurally similar but sequence unrelated molecule interleukin-34 (IL-34) are two endogenous ligands of CSF1R, which is exclusively expressed by macrophages and microglia. Colony stimulating factor 1 (CSF-1), also known as macrophage colony stimulating factor (M-CSF) is a cytokine produced by a variety of cells. CSF-1 is composed of two "monomer" polypeptides, which form a biologically active dimeric CSF-1 protein. CSF-1 exists in at least three mature forms due to alternative RNA splicing, proteolytic processing of protein precursors and posttranslational modifications including glycosylation and addition of proteoglycan (see, Cerretti D P et al. 1988, Mol Immunol, 25(8), 761; Pixley F J and Stanley E R, 2004, Trends in Cell Biology, 14(11) 628-38; Douglass, T G et al, 2008, Int Immunopharmacol, 8, 1354-76). The various forms of CSF-1 protein include two secreted molecules, one that is glycosylated, the other comprised of a longer amino terminal sequence and proteoglycan modification. Another variant is a transmembrane (TM) molecule that is glycosylated but has no proteoglycan moieties. This membrane form can be shed via proteolytic cleavage to release an active, soluble molecule. All forms are produced as precursor polypeptides having a 32 amino acid signal sequence at the amino terminus, a putative transmembrane region of approximately 23 amino acids near the carboxyl terminus and a short cytoplasmic COOH-terminal tail. The precursor peptides are subsequently processed by amino terminal and carboxyl terminal proteolytic cleavages to produce the mature forms of CSF-1 with residues 1-149 being identical and constituting the receptor binding domain. In vivo, CSF-1 monomers are glycosylated, and dimerized via disulfide-linkage. CSF-1 belongs to a group of biological agonists that promote the production of blood cells. Specifically, it acts as a growth, differentiation and survival factor for bone marrow progenitor cells of the mononuclear phagocyte lineage. Further, CSF-1 stimulates the survival, proliferation and function of macrophages via a specific receptor on responding cells. Other experiments indicated that the macrophage colony-stimulating factor (M-CSF) alters the phenotype of adult human microglia cultured after biopsy from patients with intractable TLE (Smith et al., 2013). Other recent data indicate that mutations in CSF-1R gene cause hereditary diffuse leukoencephalopathies that are associated with seizures and epilepsy (Rademakers et al., 2011; Guerreiro et al., 2013).

The CSF-1 receptor (CSF-1R) is also referred to as the c-fms gene product or CD115. CSF-1R is a 165 kDa type 1 TM glycoprotein belonging to the type III receptor tyrosine kinase family. Further, the CSF-1 receptor is responsible for regulation of proliferation, differentiation, and survival of mononuclear phagocytic cells, including microglia. Mice lacking CSF-1R display reduced number of macrophages in peripheral tissues. Importantly, CSF-1R-deficient mice also lack microglia in the brain, which is associated with a lethal phenotype. In fact, microglia are the only cells in the brain that expresses the CSF-1R under normal conditions, although low levels of CSF-1R have been observed in cultured neurons. Binding of the ligand CSF-1 to the CSF-1R results in the phosphorylation of the receptor on one or more tyrosine residues, through the action of the tyrosine kinase domain. This phosphorylation can be detected because antibodies are available that bind to the receptor only after phosphorylation (for example Phospho-M-CSF-Receptor (Tyr546) antibody #3083 from Cell Signaling Technology).

Antibodies to CSF-1R are known in the art. Sherr, C. J. et al., Blood 73 (1989) 1786-1793 describes antibodies against CSF-1 R that inhibit the CSF-1 activity (Sherr, C. J. et al., Blood 73 (1989) 1786-1793). WO09/026303 discloses anti-CSF-1R antibodies which bind to human CSF-1R and in vivo mouse tumour models using an anti-murine CSF-1R antibody. WO11/123381 discloses anti-CSF-1R antibodies which internalize CSF-1R and have ADCC activity. WO11/123381 discloses in vivo mouse tumour models using an anti-murine CSF-1R antibody. WO11/140249 discloses anti- CSF-1R antibodies which block binding of CSF-1 to CSF-1R which are stated to be useful in the treatment of cancer. WO09/112245 discloses an anti-CSF-1R IgG1 antibody which inhibits CSF-1 binding to CSF-1R and is stated to be useful in the treatment of cancer, inflammatory bowel disease and rheumatoid arthritis. WO11/131407 discloses an anti-CSF-1R antibody which inhibits CSF-1 binding to CSF-1R and is stated to be useful in the treatment of bone loss and cancer. WO11/107553 discloses an anti-CSF-1R antibody which inhibits CSF-1 binding to CSF-1R and is stated to be useful in the treatment of bone loss and cancer. WO11/070024 discloses anti-CSF-1R antibodies which bind to human CSF-1R fragment delD4. WO15/028455 discloses an anti-CSF-1R antibody which inhibits CSF-1 binding to CSF-1R and is stated to be useful in the treatment of fibrosis and cancer.

However, there still exists severe limitations and concerns associated with blood-brain barrier (BBB) permeability of large biological molecules, like for example antibodies. So far, modulating brain inflammation by large molecules or antibodies has not been proven successful. Rather, it has been shown that etanercept, a clinically used recombinant TNF receptor fused to the IgG1 antibody, does not cross the blood-brain barrier (BBB) and does not affect TNF-α-driven inflammation in the brain after systemic administration in rodents (Zhou et al., 2011). There still exist significant doubts about the potential for centrally-mediated therapeutic effects of systemically injected antibodies, which would be the typical route of administration in the clinic. This is particularly problematic for an anti-CSF1R antibody, because the CSF1R is also expressed in the endothelial cells of brain capillaries and activation of this receptor by its natural ligand, IL-34, has been shown to restore the BBB integrity and limit its permeability (Jin et al., 2014).

Consequently, there is currently still a high unmet medical need for improved, safe and efficacious therapeutic treatment and/or prophylaxis of neurologic disease. Accordingly, it is an object of the present invention to provide a new method of treatment of neurologic disease, more specifically epilepsy.

SUMMARY OF THE DISCLOSURE

In one aspect the present invention provides an inhibitor of CSF-1R activity for use in the treatment and/or prophylaxis of neurologic diseases.

In one aspect the inhibitor of present invention is a nucleic acid. In a further aspect the inhibitor of present invention is an antibody or functionally active fragment or derivative thereof.

In one aspect the present invention presents results indicating that systemic injection of anti-CSF-1R antibody in animal model of temporal lobe epilepsy (TLE) is able to modulate microglia function, evidenced by change in expression of microglial genes. Consequently, the presented results provide a potent viable therapeutic biological entity (NBE) as inhibitor of CSF-1R activity for use in treatment and/or prophylaxis of neurologic diseases.

Hence, the present invention addresses the unmet needs and provides an inhibitor of CSF-1R activity for use in the treatment and/or prophylaxis of neurologic disease. The present invention further provides an inhibitor of CSF-1R activity for use in the treatment and/or prophylaxis of epilepsy, epileptogenesis, seizures and convulsions.

In one aspect of the present invention there is provided the use of an inhibitor of CSF-1R activity, for the manufacture of a medicament for the treatment and or prophylaxis of neurologic disease.

The present invention further provides a pharmaceutical composition comprising an inhibitor of CSF-1R activity. Moreover, the present invention provides a method for the treatment and/or prophylaxis of a human subject suffering from or at risk of developing a neurologic disease comprising administering a therapeutically effective amount of an inhibitor of CSF-1R activity.

DETAILS OF THE DISCLOSURE

In one embodiment of the present invention the inhibitor of CSF-1R activity provided for use in the treatment and/or prophylaxis of neurologic diseases is a nucleic acid. In a further aspect the inhibitor of present invention is an antibody or functionally active fragment or derivative thereof.

In the present invention, the term "neurologic disease" refers to the following diseases: Alzheimer's disease, Amyotrophic lateral sclerosis (ALS), Angelman syndrome, Attention deficit hyperactivity disorder, Autism spectrum, Bipolar disorder, Brain damage, Brain injury, Brain tumor, Central pain syndrome, Cerebral atrophy, Chronic inflammatory demyelinating polyneuropathy (CIDP), Chronic pain, Complex regional pain syndrome, Creutzfeldt-Jakob disease, Dementia, Down syndrome, Dravet syndrome, Encephalitis, Essential tremor, Friedreich's ataxia, Fragile X syndrome, Fragile X-associated tremor/ataxia syndrome (FXTAS), Head injury, Headache, Herpes zoster, Huntington's disease, Hypoxia, Immune-Mediated encephalomyelitis, Infantile spasms, Intracranial hypertension, Lafora disease, Landau-Kleffner syndrome, Lennox-Gastaut syndrome, Leukodystrophy, Leukoencephalopathy with vanishing white matter, Lewy body dementia, Lissencephaly, Lyme disease—Neurological Sequelae, Megalencephaly, Meningitis, Microcephaly, Migraine, Mini-stroke (transient ischemic attack), Motor Neurone Disease—see amyotrophic lateral sclerosis, Multi-infarct dementia, Multiple sclerosis, Myoclonic Encephalopathy of infants, Myoclonus, Neurological manifestations of AIDS, Neurological sequelae of lupus, Neuronal ceroid lipofuscinosis, Neuropathy, Niemann-Pick disease, Ohtahara syndrome, Parkinson's disease, Paraneoplastic diseases, Primary Lateral Sclerosis, Prion diseases, Progressive multifocal leukoencephalopathy, Progressive Supranuclear Palsy, Rasmussen encephalitis, Restless legs syndrome, Rett syndrome, Stiff-person syndrome, Stroke, Transient ischemic attack, Traumatic brain injury, Tremor, Tuberous sclerosis, Unverricht-Lundborg disease, Uncinate epilepsy, West syndrome, Wilson's disease.

Preferred examples of neurologic diseases include Angelman syndrome, Attention deficit hyperactivity disorder, Autism spectrum, Brain injury, Brain tumor, Creutzfeldt-Jakob disease, Down syndrome, Dravet syndrome, Encephalitis, Fragile X syndrome, Fragile X-associated tremor/ataxia syndrome (FXTAS), Head injury, Herpes zoster, Hypoxia, Immune-Mediated encephalomyelitis, Infantile spasms, Lafora disease, Landau-Kleffner syndrome, Lennox-Gastaut syndrome, Leukodystrophy, Leukoencephalopathy with vanishing white matter, Lissencephaly, Lyme disease—Neurological Sequelae, Meningitis, Multiple sclerosis, Myoclonic Encephalopathy of infants, Myoclonus, Neurological sequelae of lupus, Ohtahara syndrome, Prion diseases, Rasmussen encephalitis, Rett syndrome, Traumatic brain injury, Tuberous sclerosis, Unverricht-Lundborg disease, Uncinate epilepsy or West syndrome.

In the present invention treatment of neurologic disease preferably pertain to epilepsy, epileptogenesis, seizure disorders and convulsion.

Examples of epilepsy syndromes arranged by age at onset are neonatal period (benign familial neonatal epilepsy (BFNE), early myoclonic encephalopathy (EME), ohtahara syndrome), infancy (epilepsy of infancy with migrating focal seizures, west syndrome, myoclonic epilepsy in infancy (MEI), benign infantile epilepsy, benign familial infantile epilepsy, dravet syndrome, myoclonic encephalopathy in nonprogressive disorders), childhood (febrile seizures plus (FS+), which can start in infancy, panayiotopoulos syndrome, epilepsy with myoclonic atonic (previously astatic) seizures, benign epilepsy with centrotemporal spikes (BECTS), autosomal-dominant nocturnal frontal lobe epilepsy (ADNFLE), late onset childhood occipital epilepsy (Gastaut type), epilepsy with myoclonic absences, lennox-Gastaut syndrome, epileptic encephalopathy with continuous spike-and-wave, during sleep (CSWS)b, landau-Kleffner syndrome (LKS), childhood absence epilepsy (CAE)), adolescence/adult (juvenile absence epilepsy (JAE), juvenile myoclonic epilepsy (JME), epilepsy with generalized tonic-clonic seizures alone, progressive myoclonus epilepsies (PME), autosomal dominant epilepsy with auditory features (ADEAF), other familial temporal lobe epilepsies), less specific age relationship (familial focal epilepsy with variable foci (childhood to adult), reflex epilepsies), distinctive constellations (mesial temporal lobe epilepsy with or without hippocampal sclerosis (MTLE with or without HS), Rasmussen syndrome, gelastic seizures with hypothalamic hamartoma, hemiconvulsion-hemiplegia-epilepsy, epilepsies that do not fit into any of these diagnostic categories can be distinguished first on the basis of the presence or absence of a known structural or metabolic condition (presumed cause) and then on the basis of the primary mode of seizure onset (generalized vs. focal)), epilepsies attributed to and organized by structural-metabolic causes (malformations of cortical development (hemimegalencephaly, heterotopias, etc.), neurocutaneous syndromes (tuberous sclerosis complex, Sturge-Weber, etc.), tumor, infection, trauma, angioma, perinatal insults, stroke), epilepsies of unknown cause and conditions with epileptic seizures that are traditionally not diagnosed as a form of epilepsy per se (benign neonatal seizures (BNS), febrile seizures (FS)).

In a more preferred embodiment, the present invention provides an inhibitor for use in treatment and/or prophylaxis of epilepsy wherein the type of epilepsy is selected from the group comprising generalized seizures, focal seizures and seizures of unknown origin. In a most preferred embodiment the present invention provides an inhibitor for use in treatment and/or prophylaxis of temporal lobe epilepsy (TLE).

The term 'CSF-1R activity' as used herein refers to the spectrum of activity understood in the art for CSF-1R, in particular the activity of human CSF-1R and isoforms thereof, for example 1, 2, 3 or all isoforms. For example, binding of ligand to the receptor induces phosphorylation of CSF-1R at specific tyrosine residues (Bourette R P and Rohrschneider L R, 2000, Growth Factors 17: 155-166) and the ensuing cascade of signal transduction events can mediate cell migration, survival, differentiation and proliferation (Suzu S et al, 1997, J Immunol, 159, 1860-7; Yeung Y-G and Stanley E R, 2003, Mol Cell Proteomics, 2, 1143-55; Yu W et al 2008, J Leukoc Biol84(3), 852-63). Expression in transfected cells of mutant CSF-1R receptor molecules comprising phenylalanine residues in place of selected tyrosine residues revealed the association of specific tyrosine residues with cellular outcomes such as survival, proliferation and morphology (Yu et al J Leukoc Biol 2008 September 84(3): 852-863). Proteomic approaches and immunoblotting techniques using anti-phosphotyrosine antibodies together with molecule specific antibodies, have identified a number of the intracellular molecules involved in mediating these cell functions following ligand stimulation of the receptor (Yeung Y-G et al, 1998, J Biol Chem. 13, 273(46): 17128-37; Husson H et al, 1997, Oncogene 15, 14(19): 2331-8.

An inhibitor of CSF-1R activity according to the present invention is an agent that interferes with, for example reduces/inhibits, blocks or competes with the activity of CSF-1R, in particular the activity of CSF-1R in neurologic disease. Particularly preferred are agents which interfere with the activity of CSF-1R in Alzheimer's disease, Parkionson's disease, epilepsy, epileptogenesis, seizures and convulsions. Inhibitors according to the present invention may partially or completely inhibit CSF-1R activity. Inhibitors of use in the present invention include without limitation, inhibitors that are capable of interacting with (e.g. binding to, or recognising) IL-34, CSF-1 or the CSF-1 receptor (CSF-1R) or a nucleic acid molecule encoding IL-34, CSF-1 or CSF-1R, or are capable of inhibiting the expression of IL-34, CSF-1 or CSF-1 R or are capable of inhibiting the interaction between CSF-1R and CSF-1 and/or IL-34. Such inhibitors may be, without limitation, antibodies, nucleic acids (e.g. DNA, RNA, antisense RNA and siRNA), carbohydrates, lipids, proteins, polypeptides, peptides, peptidomimetics and other drugs.

Examples, of suitable inhibitors include, but are not limited to, a synthetic functional fragment of the CSF-1 receptor that binds to CSF-1 and interferes with binding to the native CSF-1 receptor, a synthetic functional fragment of CSF-1 that binds to CSF-1 receptor and interferes with binding to the native CSF-1 receptor, a synthetic functional fragment of IL-34 that binds to CSF-1 receptor and interferes with binding to the native CSF-1 receptor, an antibody that binds to CSF-1 or IL-34 or to the CSF-1 receptor and interferes with CSF-1 receptor-ligand interaction, an antisense nucleic acid molecule that specifically hybridizes to mRNA encoding CSF-1, IL-34 or the CSF-1 receptor or other drug which inhibits the activity of IL-34, CSF-1 or CSF-1R.

Inhibitors of CSF-1 receptor activity are known in the art as are methods of identifying and producing such inhibitors. Neutralising anti-CSF-1 antibodies have been described, for example by Weir et al., 1996, J Bone Miner. Res. 1 1, 1474-1481 and Haran-Ghera et al, 1997, Blood, 89, 2537-2545, which also describes anti-CSF-1R antibodies. Antisense antagonists of CSF-1 have also been described (EP1223980).

Agents that may be suitable inhibitors can be selected from a wide variety of candidate agents. Examples of candidate agents include but are not limited to, nucleic acids (e.g. DNA and RNA), carbohydrates, lipids, proteins, polypeptides, peptides, peptidomimetics and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or libraries of compounds (Lam, 1997, Anticancer Drug Des. 12:145; U.S. Pat. Nos. 5,738,996; and 5,807,683).

Examples of suitable methods based on the present description for the synthesis of molecular libraries can be found in the art, for example in: DeWitt et al, 1993, Proc. Natl. Acad. Sci. USA 90:6909; Erb et al, 1994, Proc. Natl. Acad. Sci. USA 91:11422; Zuckermann et al, 1994, J. Med. Chem. 37:2678; Cho et al, 1993, Science 261:1303; Carrell et al, 1994, Angew. Chem. hit. Ed. Engl. 33:2059; Carell et al, 1994, Angew. Chem. Int. Ed. Engl. 33:2061; and Gallop et al, 1994, J. Med. Chem. 37:1233.

Libraries of compounds maybe presented, for example, in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al, 1992, Proc. Natl. Acad. Sci. USA 89:1865-1869) or phage (Scott and Smith, 1990, Science 249:386-390; Devlin, 1990, Science 249:404-406; Cwirla et al, 1990, Proc. Natl. Acad. Sci. USA 87:6378-6382; and Felici, 1991, J. Mol. Biol. 222:301-310).

In one example, the inhibitor for use in the present invention may be a nucleic acid. In particular CSF-1, IL-34 or CSF-1R nucleic acid molecules may be used as anti-sense molecules, to alter the expression of their respective polypeptides by binding to complementary nucleic acids. CSF-1, IL-34 or CSF-1R nucleic acids may be obtained using standard cloning techniques from for example genomic DNA or cDNA or can be synthesised using well known and commercially available techniques. The CSF-1, IL-34 or CSF-1R nucleic acids may contain one or more nucleotide substitutions, additions or deletions into the nucleotide sequence of a CSF-1, IL-34 or CSF-1R nucleic acid. Standard techniques known to those of skill in the art can be used to introduce mutations, including, for example, site-directed mutagenesis and PCR-mediated mutagenesis. An antisense nucleic acid according to the present invention includes a CSF-1, IL-34 or CSF-1R nucleic acid capable of hybridising by virtue of some sequence complementarity to a portion of an RNA (preferably mRNA) encoding the respective polypeptide. The antisense nucleic acid can be complementary to a coding and/or non-coding region of an mRNA encoding such a polypeptide. Most preferably, the antisense nucleic acids result in inhibition of the expression of the CSF-1, IL-34 or CSF-1R polypeptide. The present invention also provides an inhibitor of CSF-1R activity for use in the treatment and/or prophylaxis of a human subject suffering from or at risk of developing neurologic disease, comprising administering to the subject a therapeutically effective amount of an inhibitor of CSF-1R activity, which is an isolated DNA, comprising at least eight nucleotides (for example 15 to 22 nucleotides, such as 15, 16, 17, 18, 19, 20, 21 or 22 nucleotides) that are antisense to a gene or cDNA encoding a CSF-1, IL-34 or CSF-1R polypeptide.

In one embodiment, the inhibitor for use in the treatment and/or prophylaxis of neurologic disease is an antibody that interacts with (i.e. binds to or recognises) CSF-1 or IL-34. In another embodiment the antibody selectively interacts with CSF-1 or IL-34. Selectively interacting with (e.g. recognising or binding to) means that the antibody has a greater affinity for CSF-1 or IL-34 polypeptides than for other polypeptides. Examples of suitable antibodies are those that inhibit the activity of CSF-1 or IL-34 by binding to CSF-1 or IL-34 in such a manner as to prevent it being biologically active, for example by preventing the binding of CSF-1 or IL-34 to its receptor.

One embodiment of the present invention provides an inhibitor for use in the treatment and/or prophylaxis of neurologic disease, wherein the antibody or fragment or derivative thereof binds to CSF-1R. Most preferably, an inhibitor for use in the treatment and/or prophylaxis of neurologic disease is an antibody that interacts with (i.e. binds to or recognises) CSF-1R and inhibits the activity of CSF-1R. In one embodiment the antibody selectively interacts with CSF-1R. Selectively interacting with (e.g. recognising or binding to) means that the antibody has a greater affinity for CSF-1R polypeptide than for other polypeptides. Examples of suitable antibodies are those that inhibit the activity of CSF-1R by binding to CSF-1R in such a manner as to prevent it being biologically active.

In one embodiment the antibody recognises isoforms of CSF-1R, for example human CSF-1R and isoforms thereof.

In one embodiment the inhibitor of CSF-1R activity for use in the treatment and/or prophylaxis of neurologic diseases according to present invention blocks binding of CSF-1 to the receptor CSF-1R.

"Blocking" as employed herein refers to physically blocking such as occluding the receptor but will also include where the antibody or fragments binds an epitope that causes, for example a conformational change which means that the natural ligand to the receptor no longer binds. (referred to herein as allosteric blocking or allosteric inhibition).

In one embodiment the antibodies of the present disclosure bind all isotypes of CSF-1R, for example those with variations in the ECD domain, such as V23G, A245S, H247P, V279M and combinations of two, three or four of said variations. CSF-1 and IL-34 are both ligands for CSF-1R and the antibodies for use in the invention preferably inhibit the activity both CSF-1 and IL-34 in a functional cellular screen. The antibodies for use according to the present invention also preferably do not cause CSF-1R activation and/or CSF-1R internalisation.

Assays suitable for determining the ability of an antibody to block CSF-1R are described in the Examples herein, see Example 2.

BIAcore is an example of an assay employed to measure binding kinetics, ELISA assays or cell based assays employing monocytes or THP-1 cells may also be useful. CSF-1 and IL-34 are both ligands for CSF-1R and the anti-CSF-1R antibody may block binding of CSF-1 or IL-34 to CSF-1R but preferably blocks binding of both CSF-1 and IL-34 to CSF-1R. The anti-CSF-1R antibody also preferably does not cause CSF-1R activation or CSF-1R internalisation. Assays suitable for determining the ability of an antibody to cause CSF-1R activation or CSF-1R internalisation are described in the Examples, see Example 2 which describes an assay measuring CSF-1 dependent proliferation.

CSF-1, IL-34 or CSF-1R polypeptides or cells expressing said polypeptides can be used to produce antibodies which specifically recognise said polypeptides.

The CSF-1, IL-34 and CSF-1 R polypeptides may be 'mature' polypeptides or biologically active fragments or derivatives thereof. Preferably the CSF-1 polypeptide contains amino acids 1-149 believed to be important for biological activity.

CSF-1R as employed herein refers to the protein named CSF-1R (as shown in SEQ ID NO:11), isoforms thereof and biologically active fragments thereof. SEQ ID NO:11 shows the full 972 amino acid sequence of human CSF1-R, where residues 1-19 are the predicted signal peptide. Preferably the CSF-1R polypeptide contains amino acids 20-517 of the human, representing the predicted extracellular region of the CSF-1R sequence. Alternative forms of CSF-1R are known. In one embodiment CSF-1R is human protein or an isoform thereof. Generally an antibody employed in the present invention will be directed to the extracellular domain of CSF-1R. Human CSF-1R as shown in SEQ ID NO:15 is registered in the UniProt database under P07333.

CSF-1 and CSF-1R polypeptides may be prepared by processes well known in the art from genetically engineered host cells comprising expression systems or they may be recovered from natural biological sources. In one embodiment the sequence shown in SEQ ID NO:15 may be transfected into a suitable cell line and the polypeptide expressed on the cell surface. The amino acid fragment may be fused to a GPI-anchor to facilitate said expression. The cells may then be employed to immunize hosts.

In the present application, the term "polypeptides" includes peptides, polypeptides and proteins. These are used interchangeably unless otherwise specified. CSF-1, IL-34 or CSF-1R polypeptides may in some instances be part of a larger protein such as a fusion protein for example fused to an affinity tag.

Antibodies generated against these polypeptides may be obtained by administering the polypeptides or cells expressing the same to an animal, preferably a non-human animal, using well-known and routine protocols, see for example Handbook of Experimental Immunology, D. M. Weir (ed.), Vol 4, Blackwell Scientific Publishers, Oxford, England, 1986. Many warm-blooded animals, such as rabbits, mice, rats, sheep, cows or pigs may be immunized. However, mice, rabbits, pigs and rats are generally preferred.

In one embodiment the inhibitor provided by the present invention is an antibody or functionally active fragment or derivative thereof. In another embodiment the inhibitor provided by the present invention is a monoclonal or polyclonal antibody. In another embodiment the inhibitor provided by the present invention is an antibody or fragment or derivative thereof which is chimeric, humanized or human antibody.

Monoclonal antibodies may be prepared by any method known in the art such as the hybridoma technique (Kohler and Milstein, 1975, Nature, 256:495-497), the trioma technique, the human B-cell hybridoma technique (Kozbor et al, 1983, Immunology Today, 4:72) and the EBV-hybridoma technique (Cole et al, Monoclonal Antibodies and Cancer Therapy, p 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al, 1996, Proc. Natl. Acad. Sci. USA 93(15): 7843-7848, WO92/02551 and WO2004/051268 and WO2004/106377.

Specific as employed herein is intended to refer to an antibody that only recognises the antigen to which it is specific or an antibody that has significantly higher binding affinity to the antigen to which it is specific compared to binding to antigens to which it is non-specific, for example at least 5, 6, 7, 8, 9, 10 times higher binding affinity.

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al, 1983, Nature 305:537-539; WO 93/08829, Traunecker et al, 1991, EMBO J. 10:3655-3659). Multi-valent antibodies may comprise multiple specificities or may be monospecific (see for example WO 92/22853).

As used herein, the term 'humanized antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody) (see, e.g. U.S. Pat. No. 5,585,089; WO91/09967). For a review, see Vaughan et al, Nature Biotechnology, 16, 535-539, 1998.

In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

In a humanized antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

When the CDRs or specificity determining residues are grafted, any appropriate acceptor variable region framework sequence may be used having regard to the class/type of the donor antibody from which the CDRs are derived, including mouse, primate and human framework regions.

Suitably, the humanized antibody has a variable domain comprising human acceptor framework regions as well as one or more of CDRs. Thus, provided in one embodiment is humanized antibody which binds human CSF-1, IL-34 or CSF-1R wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at vbase.mrc-cpe.cam.ac.uk/.

In a humanized antibody of the present invention, the acceptor heavy and light chains do not necessarily need to be derived from the same antibody and may, if desired, comprise composite chains having framework regions derived from different chains.

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al (Eur. J. Immunol. 1994, 24:952-958), Persic et al. (Gene, 1997 187 9-18), Burton et al (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409;

5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies to CSF-1, IL-34 or CSF-1R polypeptides. Also, transgenic mice, or other organisms, including other mammals, may be used to express humanized antibodies.

An embodiment of the present provides an inhibitor of CSF-1R activity which is an antibody or fragment or derivative thereof which is bispecific or multispecific. In a further embodiment of the present invention, the antibody for use in treatment and/or prophylaxis of neurologic disease may be selected from the group comprising a complete antibody molecule having full length heavy and light chains or a fragment thereof selected from the group comprising a Fab, modified Fab, Fab', modified Fab', F(ab')$_2$, Fv, single domain antibodies (e.g. VH or VL or VHH), scFv, bi, tri or tetravalent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217).

The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

In one embodiment the antibody is provided as CSF-1, IL-34 or CSF-1R binding antibody fusion protein which comprises an immunoglobulin moiety, for example a Fab or Fab' fragment, and one or two single domain antibodies (dAb) linked directly or indirectly thereto, for example as described in WO2009/040562, WO2010/035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

Antibody fragments and methods of producing them are well known in the art, see for example Verma et al, 1998, Journal of Immunological Methods, 216, 165-181. Particular examples of antibody fragments for use in the present invention are Fab' fragments which possess a native or a modified hinge region. A number of modified hinge regions have already been described, for example, in U.S. Pat. No. 5,677,425, WO99/15549, and WO98/25971 and these are incorporated herein by reference Further examples of particular antibody fragments for use in the present invention include those described in international patent applications PCT/GB2004/002810, PCT/GB2004/002870 and PCT/GB2004/002871 (all filed on 1 Jul. 2004). In particular the modified antibody Fab fragments described in International patent application PCT/GB2004/002810 are preferred.

In one embodiment the antibody heavy chain comprises a CH1 domain and the antibody light chain comprises a CL domain, either kappa or lambda.

In one embodiment the antibody heavy chain comprises a CH1 domain, a CH2 domain and a CH3 domain and the antibody light chain comprises a CL domain, either kappa or lambda.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

In a specific embodiment, the antibody of the present invention is an IgG2 or IgG4 antibody. It will be appreciated that sequence variants of these constant region domains may also be used. For example IgG4 molecules in which the serine at position 241 has been changed to proline as described in Angal et al., 1993, Molecular Immunology, 1993, 30:105-108 may be used. A single amino acid substitution abolishes the heterogeneity of chimeric mouse/human (IgG4) antibody. Mol. Immunol. 30:105-108) describes a site directed mutagenesis approach to minimize half-molecule formation of IgG4 antibodies. n this report, a single amino acid substitution within the core hinge, S241P, resulted in substantially less half-molecule formation. Accordingly, in the embodiment where the antibody is an IgG4 antibody, the antibody may include the mutation S241P. Differential ADCC induction by different IgG isotypes is dependent on the affinity of these residues to FcγRs. In humans, IgG1 and IgG3 are known to induce effector functions whereas IgG2 and IgG4 induce effector functions weakly. In a preferred embodiment the antibody for use in the present invention is an IgG2 or IgG4 antibody which induces effector functions weakly, including ADCC. It is particularly preferred for the antibody for use in treating neurologic disease in the present invention to have limited effector function because the use of an antibody with effector function may cause enhanced depletion of cells expressing CSF-1R which has potential to add to side effects in the patient.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In another embodiment, inhibitors of CSF-1R activity may be used in the treatment and/or prophylaxis of neurologic disease is an antibody or fragment or derivative thereof which crosses the blood-brain-barrier (BBB) reaching in the brain a therapeutically effective amount sufficient for the treatment and/or prophylaxis of a patient suffering from neurologic disease.

The term "therapeutically effective amount" as used herein refers to an amount of a therapeutic agent needed to treat, ameliorate or prevent a targeted disease or condition, or to exhibit a detectable therapeutic, pharmacological or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg.

In another embodiment the inhibitor for use in the treatment and/or prophylaxis of neurologic disease is an antibody or fragment or derivative thereof comprises a heavy chain and a light chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3.

The present invention also provides an inhibitor for use in the treatment and/or prophylaxis of neurologic disease is, wherein the antibody or fragment or derivative thereof comprises a heavy chain and a light chain, wherein the variable domain of the light chain comprises at least one of a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3.

In another embodiment the inhibitor for use in the treatment and/or prophylaxis of neurologic disease is an inhibitor comprising a heavy chain and a light chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3 and wherein the variable domain of the light chain comprises at least one of a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3.

In another embodiment the inhibitor for use in the treatment and/or prophylaxis of neurologic disease is an inhibitor wherein the heavy chain comprises the sequence given in SEQ ID NO:9.

The present invention also provides an inhibitor for use in the treatment and/or prophylaxis of neurologic disease wherein the light chain comprises the sequence given in SEQ ID NO:7.

The present invention also provides an inhibitor for use in the treatment and/or prophylaxis of neurologic disease having a heavy chain comprising the sequence given in SEQ ID NO:9 and a light chain comprising the sequence given in SEQ ID NO:7.

In one aspect of the present invention, there is provided an anti-CSF-1R antibody or binding fragment or derivative thereof, wherein the variable domain of the heavy chain comprises three CDRs and the sequence of CDR-H1 has at least 60%, 70%, 80%, 90% or 95% identity or similarity to the sequence given in SEQ ID NO:4, the sequence of CDR-H2 has at least 60%, 70%, 80%, 90% or 95% identity or similarity to the sequence given in SEQ ID NO:5 and the sequence of CDR-H-3 has at least 60%, 70%, 80%, 90% or 95% identity or similarity to the sequence given in SEQ ID NO:6. Preferably, the anti-CSF-1R antibody or binding fragment thereof, additionally comprising a light chain, wherein the variable domain of the light chain comprises three CDRs and the sequence of CDR-L1 has at least 60%, 70%, 80%, 90% or 95% identity or similarity to the sequence given in SEQ ID NO:1, the sequence of CDR-L2 has at least 60%, 70%, 80%, 90% or 95% identity or similarity to the sequence given in SEQ ID NO:2 and the sequence of CDR-L3 has at least 60% identity or similarity to the sequence given in SEQ ID NO:3. In one embodiment a variable regions is provided with at least 60%, 70%, 80%, 90% or 95% identity or similarity to a variable region sequence disclosed herein.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In an embodiment of present invention the inhibitor for use in the treatment and/or prophylaxis of neurologic disease is an inhibitor wherein the antibody or fragment or derivative thereof having a binding affinity $[K_D]$ for human CSF-1R of 10 pM or less than 10 pM determined according to BIAcore method.

In an embodiment of present invention the inhibitor for use in the treatment and/or prophylaxis of neurologic disease is an inhibitor wherein the antibody or fragment or derivative thereof cross-blocks the binding of an anti-CSF-1R antibody with an affinity [$K_D$] of 100 pM or less determined according to BIAcore method.

The antibody or fragment or derivative thereof of the present invention suitably have a high binding affinity. Affinity may be measured using any suitable method known in the art, including techniques such as surface plasmon resonance, for example BIAcore, using isolated natural or recombinant CSF-1R or a suitable fusion protein/polypeptide. For example affinity may be measured using recombinant human CSF-1R extracellular domain. Recombinant human CSF-1R extracellular domain for use may be a monomer. Suitably the antibody molecules for use of the present invention have a binding affinity for isolated human CSF-1R of about 1 nM or less than 1 nM. In one embodiment the antibody molecule of the present invention has a binding affinity of about 500 pM or lower. In one embodiment the antibody molecule of the present invention has a binding affinity of about 250 pM or lower. In one embodiment the antibody molecule of the present invention has a binding affinity of about 200 pM or lower. In one embodiment the present invention provides an anti-CSF-1R antibody with a binding affinity of about 100 pM or lower. In one embodiment the present invention provides a humanized anti-CSF-1R antibody with a binding affinity of about 100 pM or lower, preferably about 10 pM or lower, more preferably about 5 pM or lower. In another embodiment the present invention provides a humanized anti-CSF-1R antibody with a binding affinity of about 100 pM or lower, preferably about 10 pM or lower, more preferably about 5 pM or lower.

The lower the numerical value of the affinity the higher the affinity of the antibody or fragment for the antigen.

In an embodiment of present invention the inhibitor for use in the treatment and/or prophylaxis of neurologic disease is an inhibitor wherein the antibody or fragment or derivative thereof cross-blocks the binding by binding the same epitope as the antibody which it blocks. Examples of suitable cross-blocking assays are described in WO15/028455.

The present invention also provides an inhibitor for use in the treatment and/or prophylaxis of neurologic disease wherein the antibody or fragment or derivative thereof competes with the antibody or fragment or derivative thereof of an anti-CSF-1R antibody for binding to the extracellular domain of human c-fms of SEQ ID NO: 15.

The term "compete" when used in the context of antigen binding proteins (e.g. neutralizing antigen binding proteins or neutralizing antibodies) that compete for the same epitope means competition between antigen binding proteins is determined by an assay in which the antigen binding protein (e.g., antibody or immunologically functional fragment or derivative thereof) under test prevents or inhibits specific binding of a reference antigen binding protein (e.g., a ligand, or a reference antibody) to a common antigen (e.g., c-fms or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, *Methods in Enzymology* 2:242-253); solid phase direct biotin-avidin EIA (see, e.g., Kirkland et al., 1986, *J Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176: 546-552); and direct labeled RIA (Moldenhauer et al., 1990, *Scand. J Immunol.* 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 95%, or 97% or more.

In an embodiment of present invention the inhibitor for use in the treatment and/or prophylaxis of neurologic disease is an inhibitor which binds to the epitope of human CSF-1R as the inhibitor of a CSF-1R antibody.

In an embodiment of present invention the inhibitor for use in the treatment and/or prophylaxis of neurologic disease is an antibody which binds to the epitope of human CSF-1R.

This specific region or epitope of the human CSF-1, IL-34 or CSF-1R polypeptide can be identified by any suitable epitope mapping method known in the art in combination with any one of the antibodies provided by the present invention. Examples of such methods include screening peptides of varying lengths derived from CSF-1R for binding to the antibody of the present invention with the smallest fragment that can specifically bind to the antibody containing the sequence of the epitope recognised by the antibody. The CSF-1, IL-34 or CSF-1R peptides may be produced synthetically or by proteolytic digestion of the CSF-1, IL-34 or CSF-1R polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antibodies which bind the same epitope.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the CSF-1, IL-34 or CSF-1R antibody and fragments may be engineered to have an appropriate isoelectric point. This may lead to antibodies and/or fragments with more robust properties, in particular suitable solubility and/or stability profiles and/or improved purification characteristics.

Thus in one aspect the invention provides a humanized CSF-1, IL-34 or CSF-1R antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY (see Worldwide Website: expasy.ch/tools/pi_tool.html, and Worldwide Website: iut-arles.up.univ-mrs.fr/w3bb/d_abim/compo-p.html), may be used to predict the isoelectric point of the antibody or fragment.

It will be appreciated that the affinity of antibodies provided by the present invention may be altered using any suitable method known in the art. The present invention therefore also relates to variants of the antibody molecules of the present invention, which have an improved affinity for CSF-1, IL-34 or CSF-1R. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

If desired an antibody for use in the present invention may be conjugated to one or more effector molecule(s). An embodiment of the present invention provides an antibody for use in treatment and/or prophylaxis of neurologic disease, wherein the antibody or fragment or derivative thereof is conjugated to one or more effector molecule(s).

It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, $Lu^{177}$, $Bismuth^{213}$, $Californium^{252}$, $Iridium^{192}$ and $Tungsten^{188}$/$Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system.

Examples of suitable effector molecules of this type include polymers, albumin, albumin binding proteins or albumin binding compounds such as those described in WO05/117984.

In one embodiment a half-life provided by an effector molecule which is independent of CSF-1R is advantageous.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof.

"Derivatives" as used in present invention is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as brain, tumors or extend circulating half-life (for review see Chapman, 2002, Advanced Drug Delivery Reviews, 54, 531-545). Thus, for example, where the product is intended to leave the circulation and penetrate tissue, for example for use in the treatment of a brain or tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J.

Milton Harris (ed), Plenum Press, New York, "Poly (ethyleneglycol) Chemistry and biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

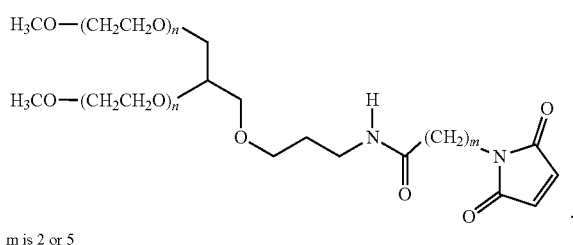

m is 2 or 5

That is to say each PEG is about 20,000 Da.

Thus in one embodiment the PEG is 2,3-Bis(methylpolyoxyethylene-oxy)-1-{[3-(6-maleimido-1-oxohexyl)amino]propyloxy} hexane (the 2 arm branched PEG, —CH$_2$)$_3$NHCO(CH$_2$)$_5$-MAL, Mw 40,000 known as SUNBRIGHT GL2-400MA3.

Further alternative PEG effector molecules of the following type:

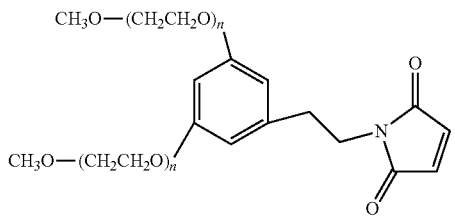

In one embodiment there is provided an antibody, such as a full length antibody, which is PEGylated (for example with a PEG described herein), attached through a cysteine amino acid residue at or about amino acid 226 in the chain, for example amino acid 226 of the heavy chain (by sequential numbering).

In one embodiment the present disclosure provides a Fab'PEG molecule comprising one or more PEG polymers, for example 1 or 2 polymers such as a 40 kDa polymer or polymers. Fab-PEG molecules according to the present disclosure may be particularly advantageous in that they have a half-life independent of the Fc fragment. In one embodiment there is provided a scFv conjugated to a polymer, such as a PEG molecule, a starch molecule or an albumin molecule. In one embodiment the antibody or fragment is conjugated to a starch molecule, for example to increase the half-life. Methods of conjugating start to a protein as described in U.S. Pat. No. 8,017,739 incorporated herein by reference.

To identify inhibitors of CSF-1R activity a number of different approaches may be taken by those skilled in the art. In one example inhibitors are identified by first identifying agents that interact with CSF-1, IL-34 or CSF-1R and subsequently testing those agents to identify those that inhibit CSF-1R activity. In one such example the agent is an antibody.

Agents or inhibitors that interact with CSF-1, IL-34 or CSF1-R may be identified using any suitable method, for example by using a cell-free or cell-based assay system where the CSF-1, IL-34 or CSF-1R polypeptide is contacted with a candidate agent and the ability of the candidate agent to interact with the polypeptide is determined. Preferably, the ability of a candidate agent to interact with a CSF-1, IL-34 or CSF-1R polypeptide is compared to a reference range or control. If desired, this assay may be used to screen a plurality (e.g. a library) of candidate agents using a plurality of CSF-1, IL-34 or CSF-1R polypeptide samples. In one example of a cell free assay, a first and second sample comprising native or recombinant CSF-1, IL-34 or CSF-1R polypeptide are contacted with a candidate agent or a control agent and the ability of the candidate agent to interact with the polypeptide is determined by comparing the difference in interaction between the candidate agent and control agent. Preferably, the polypeptide is first immobilized, by, for example, contacting the polypeptide with an immobilized antibody which specifically recognizes and binds it, or by contacting a purified preparation of polypeptide with a surface designed to bind proteins. The polypeptide may be partially or completely purified (e.g. partially or completely free of other polypeptides) or part of a cell lysate. Further, the polypeptide may be a fusion protein comprising the CSF-1, IL-34 or CSF1-R polypeptide or a biologically active portion thereof and a domain such as glutathionine-S-transferase or the Fc region of IgG1. Alternatively, the polypeptide can be biotinylated using techniques well known to those of skill in the art (e.g. biotinylation kit, Pierce Chemicals; Rockford, Ill.). The ability of the candidate agent to interact with the polypeptide can be determined by methods known to those of skill in the art for example, ELIS A, BIAcore™, Flow cytometry or fluorescent microvolume assay technology (FMAT). In another example where a cell-based assay is used, a population of cells expressing CSF-1, IL-34 or CSF-1 R is contacted with a candidate agent and the ability of the candidate agent to interact with the polypeptide is determined. Preferably, the ability of a candidate agent to interact with CSF-1, IL-34 or CSF-1 R is compared to a reference range or control. The cell, for example, can be of eukaryotic origin (e.g. yeast or mammalian) and can express the CSF-1, IL-34 or CSF-1 R polypeptide endogenously or be genetically engineered to express the polypeptide. In some instances, the CSF-1, IL-34 or CSF-1R polypeptide or the candidate agent is labelled, for example with a radioactive label (such as P, S or I) or a fluorescent label (such as fluorescein isothiocyanate, rhodamine, phycoerythrin, phycocyanin, allophycocyanin, o-phthaldehyde or fluorescamine) to enable detection of an interaction between a polypeptide and a candidate agent. Alternative methods such as ELISA, flow cytometry and FMAT may also be used. Agents which inhibit CSF-1R activity may be identified by any suitable method, for example by: (i) comparing the activity of CSF-1R in the presence of a candidate agent with the activity of said polypeptide in the absence of the candidate agent or in the presence of a control agent; and (ii) determining whether the candidate agent inhibits activity of CSF-1R. Such assays can be used to screen candidate agents, in clinical monitoring or in drug development. As described above, agents may be pre-screened where appropriate (e.g. an antibody) to identify agents that interact with CSF-1, IL-34 or CSF-1R prior to screening those agents which bind for their ability to inhibit CSF-1R activity. In one example a cell-based assay system is used to identify agents capable of inhibiting the activity of CSF-1R. In one particular example the assay used to identify inhibitors of CSF-1 activity or CSF-1R activity is the standard in vitro colony stimulating assay of Metcalf, 1970, J. Cell. Physiol. 76-89 in which CSF-1 is capable of stimulating the formation of macrophage colonies. Potential inhibitors are added to the assay and proliferation of macrophages is measured by any suitable method such as $^3$H thymidine incorporation or formazan dye conversion. Inhibition is therefore measured as a reduction in proliferation compared to controls.

In another example inhibitors of CSF-1R may down-regulate the expression of the CSF-1, IL-34 or CSF-1R polypeptide, for example antisense inhibitors. Such inhibitors may be identified by any method known in the art. In one example such inhibitors are identified in a cell-based assay system. Accordingly, a population of cells expressing a CSF-1, IL-34 or CSF-1R polypeptide or nucleic acid are contacted with a candidate agent and the ability of the candidate agent to alter expression of the CSF-1, IL-34 or CSF-1R polypeptide or nucleic acid is determined by comparison to a reference range or control. In one example, populations of cells expressing a CSF-1, IL-34 or CSF1-R polypeptide are contacted with a candidate agent or a control agent and the ability of the candidate agent to alter the expression of the CSF-1, IL-34 or CSF-1R polypeptides or nucleic acids is determined by comparing the difference in the level of expression of the CSF-1, IL-34 or CSF1-R polypeptides or nucleic acids between the treated and control populations of cells. If desired, this assay may be used to screen a plurality (e.g. a library) of candidate agents. The cell, for example, can be of eukaryotic origin (e.g. yeast or mammalian) and can express a CSF-1, IL-34 or CSF-1R polypeptide endogenously or be genetically engineered to express a CSF-1, IL-34 or CSF-1R polypeptide. The ability of the candidate agents to alter the expression of a said polypeptides or nucleic acids can be determined by methods known to those of skill in the art, for example and without limitation, by flow cytometry, radiolabelling, a scintillation assay, immunoprecipitation, Western blot analysis, Northern blot analysis or RT-PCR.

Agents that inhibit the activity of CSF-1R may be identified or further tested, for example to determine therapeutically effective amounts in one or more animal models. Examples of suitable animals include, but are not limited to, mice, rats, rabbits, monkeys, guinea pigs, dogs and cats. In one example where the agent inhibits the expression of CSF-1, IL-34 or CSF-1R, a first and second group of mammals are administered with a candidate agent or a control agent and the ability of the candidate agent to inhibit the expression of CSF-1, IL-34 or CSF-1R polypeptide or nucleic acid is determined by comparing the difference in the level of expression between the first and second group of mammals. Where desired, the expression levels of the CSF-1, IL-34 or CSF-1R polypeptides or nucleic acid in the first and second groups of mammals can be compared to the level of CSF-1, IL-34 or CSF-1R polypeptide or nucleic acid in a control group of mammals. The candidate agent or a control agent can be administered by means known in the art (e.g. orally, rectally or parenterally such as intraperitoneally or intravenously or systemically). Changes in the expression of a polypeptide or nucleic acid can be assessed by the methods outlined above.

Examples of rodent models of Alzheimer's or Parkinson's diseases have been demonstrated, for example, by Wirths et al., 2010. There microglia activation and increased expression of Iba1 in the APP/PS1KI transgenic mouse model of Alzheimer's disease have been demonstrated. Similarly, Depboylu et al., 2012 has shown strong microglia activation associated with Iba1 expression in MPTP-induced model of Parkinson's disease. Importantly, a robust microglia activation phenotype and increased Iba1 signal was observed in both rodent and non-human primate models of Parkinson's disease induced be over-expression of α-synuclein (Barkholt et al., 2012, Luk et al., 2012).

In another example, the inhibition of CSF-1R activity can be determined by monitoring an amelioration or improvement in disease symptoms, and/or a delayed onset or slowed progression of the disease. For example but without limitation, in the case of neurologic disease, like for example among others, epilepsy, Alzheimer's or Parkinson's disease this could be manifest as a reduction of markers of microglia activation or microglia cells in brain or tissue culture. Inhibition of CSF-1R activity in patients with neurologic disease can also be determined by monitoring clinical events such as reduced exacerbations, defined as a rapid deterioration in disease activity, in the absence of other causes. Thus in one embodiment employing an inhibitor of CSF-1R may provide a reduction in one or more of the follow Alzheimer's disease, Amyotrophic lateral sclerosis (ALS), Angelman syndrome, Attention deficit hyperactivity disorder, Autism spectrum, Bipolar disorder, Brain damage, Brain injury, Brain tumor, Central pain syndrome, Cerebral atrophy, Chronic inflammatory demyelinating polyneuropathy (CIDP), Chronic pain, Complex regional pain syndrome, Creutzfeldt-Jakob disease, Dementia, Down syndrome, Dravet syndrome, Encephalitis, Essential tremor, Friedreich's ataxia, Fragile X syndrome, Fragile X-associated tremor/ataxia syndrome (FXTAS), Head injury, Headache, Herpes zoster, Huntington's disease, Hypoxia, Immune-Mediated encephalomyelitis, Infantile spasms, Intracranial hypertension, Lafora disease, Landau-Kleffner syndrome, Lennox-Gastaut syndrome, Leukodystrophy, Leukoencephalopathy with vanishing white matter, Lewy body dementia, Lissencephaly, Lyme disease—Neurological Sequelae, Megalencephaly, Meningitis, Microcephaly, Migraine, Mini-stroke (transient ischemic attack), Motor Neurone Disease—see amyotrophic lateral sclerosis, Multi-infarct dementia, Multiple sclerosis, Myoclonic Encephalopathy of infants, Myoclonus, Neurological manifestations of AIDS, Neurological sequelae of lupus, Neuronal ceroid lipofuscinosis, Neuropathy, Niemann-Pick disease, Ohtahara syndrome, Parkinson's disease, Paraneoplastic diseases, Primary Lateral Sclerosis, Prion diseases, Progressive multifocal leukoencephalopathy, Progressive Supranuclear Palsy, Rasmussen encephalitis, Restless legs syndrome, Rett syndrome, Stiff-person syndrome, Stroke, Transient ischemic attack, Traumatic brain injury, Tremor, Tuberous sclerosis, Unverricht-Lundborg disease, Uncinate epilepsy, West syndrome, Wilson's disease.

In a preferred example of the present invention the inhibitor may be used in the treatment and/or prophylaxis of epilepsy, epileptogenesis, seizures and convulsions. In a further preferred embodiment of the present invention the inhibitor maybe used in the treatment and/or prophylaxis of special types of epilepsy, selected from the group comprising generalized seizures, focal seizures and seizures of unknown origin. In a more preferred embodiment of the present invention the inhibitor may be used in the treatment and/or prophylaxis of temporal lobe epilepsy (TLE).

Techniques known to physicians familiar with neurologic disease can be used to determine whether a candidate agent has altered one or more symptoms associated with the disease. A number of different models of neurologic disease are known in the art. For example, a model of neuroinflammation associated with microglia activation is based on systemic injection of lipopolysaccharide (LPS) bacterial endotoxin, which has been reported to induce microglia activation to mimic the microglia phenotype that observed in neurological diseases. This model may be used in rodent species, but a recent study demonstrated that the LPS model can be used in non-human primates, where it also associated with a robust activation of microglia activation (Hannestad et al., 2012).

Imaging techniques for neurologic diseases or microglia activation status may be Positron Emission Tomography (PET) using radioactive traces binding to the Translocator Protein (TSPO), which shows strong induction in activated microglia (Hannestad et al., 2012). TSPO is regarded as a translational marker of microglia activation, because its induction has been reported in the course of several neurological diseases such as epilepsy, Alzheimer's Parkinson's diseases (Amhaoul et al., 2014; Hommet et al., 2014; Edison et al., 2013).

One embodiment of the present invention provides an inhibitor for the treatment and/or prophylaxis of neurologic disease which is a nucleic acid.

In a further embodiment the present invention provides an inhibitor which is an isolated DNA sequence encoding the heavy and/or light chain(s) of an antibody inhibiting CSF-1R activity. In a preferred embodiment the isolated DNA sequence encoding the heavy and/or light chain(s) of an antibody or fragment or derivative thereof comprising a heavy chain and a light chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3 and wherein the variable domain of the light chain comprises at least one of a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3.

In another example, where the inhibitor is a nucleic acid this may be administered via gene therapy (see for example Hoshida, T. et al, 2002, Pancreas, 25:111-121; Ikuno, Y. 2002, Invest. Ophthalmol. Vis. Sci. 2002 43:2406-2411; Bollard, C, 2002, Blood 99:3179-3187; Lee E., 2001, Mol. Med. 7:773-782). Gene therapy refers to administration to a subject of an expressed or expressible nucleic acid, in one example this is either the CSF-1, IL-34 or the CSF-IR nucleic acid or portions thereof. Any of the methods for gene therapy available in the art can be used according to the present invention. Delivery of the therapeutic nucleic acid into a patient can be direct in vivo gene therapy (i.e. the patient is directly exposed to the nucleic acid or nucleic acid-containing vector) or indirect ex vivo gene therapy (i.e. cells are first transformed with the nucleic acid in vitro and then transplanted into the patient).

For example for in vivo gene therapy, an expression vector containing the CSF-1, IL-34 or CSF-IR nucleic acid may be administered in such a manner that it becomes intracellular, i.e. by infection using a defective or attenuated retroviral or other viral vectors as described, for example, in U.S. Pat. No. 4,980,286 or by Robbins et al, 1998, Pharmacol. Ther. 80:35-47. The various retroviral vectors that are known in the art are such as those described in Miller et al. (1993, Meth. Enzymol. 217:581-599) which have been modified to delete those retroviral sequences which are not required for packaging of the viral genome and subsequent integration into host cell DNA. Also adenoviral vectors can be used which are advantageous due to their ability to infect non-dividing cells and such high-capacity adenoviral vectors are described in Kochanek (1999, Human Gene Therapy, 10:2451-2459). Chimeric viral vectors that can be used are those described by Reynolds et al. (1999, Molecular Medicine Today, 1:25-31). Hybrid vectors can also be used and are described by Jacoby et al. (1997, Gene Therapy, 4:1282-1283). Direct injection of naked DNA or through the use of microparticle bombardment (e.g. Gene Gun®; Biolistic, Dupont) or by coating it with lipids can also be used in gene therapy. Cell-surface receptors/transfecting compounds or through encapsulation in liposomes, microparticles or microcapsules or by administering the nucleic acid in linkage to a peptide which is known to enter the nucleus or by administering it in linkage to a ligand predisposed to receptor-mediated endocytosis (See Wu and Wu, 1987, J. Biol. Chem., 262:4429-4432) can be used to target cell types which specifically express the receptors of interest. In ex vivo gene therapy, a gene is transferred into cells in vitro using tissue culture and the cells are delivered to the patient by various methods such as injecting subcutaneously, application of the cells into a skin graft and the intravenous injection of recombinant blood cells such as haematopoietic stem or progenitor cells. Cells into which a CSF-1, IL-34 or CSF-IR nucleic acid can be introduced for the purposes of gene therapy include, for example, epithelial cells, endothelial cells, keratinocytes, fibroblasts, muscle cells, hepatocytes and blood cells. The blood cells that can be used include, for example, T-lymphocytes, B-lymphocytes, monocytes, macrophages, neutrophils, eosinophils, megakaryocytes, granulocytes, haematopoietic cells or progenitor cells, microglia and the like.

An aspect of present invention is the use of an inhibitor of CSF-1R activity for the manufacture of a medicament for the treatment and/or prophylaxis of neurologic diseases. This use and the following more specific uses of the inhibitor of CSF-1R activity of the present invention comprise but are not limited to the inhibitors described above and to which all definitions provided by description also pertain.

In one embodiment of the present invention, the use of an inhibitor for the manufacture of a medicament for the treatment and/or prophylaxis of neurologic diseases comprises a nucleic acid.

In another embodiment of the present invention, the use of an inhibitor for the manufacture of a medicament for the treatment and/or prophylaxis of neurologic diseases pertain an antibody or functionally active fragment or derivative thereof. Accordingly, the use of an antibody or functionally active fragment or derivative thereof of present invention comprises a monoclonal or polyclonal antibody. Further, the use of an antibody or functionally active fragment or derivative thereof in present invention pertain a chimeric, humanized or human antibody. In one embodiment of the present invention, the use of an antibody or fragment or derivative thereof for the manufacture of a medicament for the treatment and/or prophylaxis of neurologic diseases comprises a bispecific or multispecific antibody. Accordingly, the use of an antibody or functionally active fragment or derivative thereof of present invention pertain to an antibody selected from the group comprising of a complete antibody molecule having full length heavy and light chains or a fragment thereof selected from the group comprising a Fab, modified Fab, Fab', modified Fab', F(ab')$_2$, Fv, single domain antibodies (VH or VL or VHH), scFv, bi, tri or tetra-valent antibodies, Bis-scFv, diabodies, triabodies, tetrabodies and epitope-binding fragments of any of the above.

Another embodiment of the present invention provides the use of an inhibitor for the manufacture of a medicament for the treatment and/or prophylaxis of neurologic diseases comprising an inhibitor conjugated to one or more effector molecule(s).

In another embodiment of the present invention, the use of an antibody for the manufacture of a medicament for the treatment and/or prophylaxis of neurologic diseases is provided which is an antibody which binds to CSF-1R.

Also provided by the present invention is the use of an inhibitor of CSF-1R activity, which is an antibody, wherein the antibody or fragment or derivative thereof crosses the blood-brain-barrier (BBB) reaching in the brain a therapeutically effective amount sufficient for the treatment and/or prophylaxis of a patient suffering from neurologic disease.

In another embodiment of the present invention, the use of an antibody or fragment or derivative thereof for the manufacture of a medicament for the treatment and/or prophylaxis of neurologic diseases comprises an antibody having a heavy chain and a light chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3.

Further, the present invention provides the use of an antibody or fragment or derivative thereof for the manufacture of a medicament for the treatment and/or prophylaxis of neurologic diseases, wherein the antibody or fragment or derivative thereof comprises a heavy chain and a light chain, wherein the variable domain of the light chain comprises at least one of a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3.

In another embodiment of the present invention, the use of an antibody or fragment or derivative thereof for the manufacture of a medicament for the treatment and/or prophylaxis of neurologic diseases comprises and antibody having a heavy chain and a light chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3 and wherein the variable domain of the light chain comprises at least one of a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3.

In another embodiment of the present invention, the use of an antibody or fragment or derivative thereof for the manufacture of a medicament for the treatment and/or prophylaxis of neurologic diseases comprises an antibody having a heavy chain comprising the sequence given in SEQ ID NO:9.

In another embodiment of the present invention, the use of an antibody or fragment or derivative thereof for the manufacture of a medicament for the treatment and/or prophylaxis of neurologic diseases comprises an antibody having a light chain comprising the sequence given in SEQ ID NO:7.

The present invention further provides the use of an antibody or fragment or derivative thereof for the manufacture of a medicament for the treatment and/or prophylaxis of neurologic diseases having a heavy chain comprising the sequence given in SEQ ID NO:9 and a light chain comprising the sequence given in SEQ ID NO:7.

The present invention also provides the use of an antibody or fragment or derivative thereof for the manufacture of a medicament for the treatment and/or prophylaxis of neurologic diseases, wherein the antibody or fragment or derivative thereof having a binding affinity $[K_D]$ for human CSF-1R of 10 pM or less than 10 pM.

The present invention also provides the use of an antibody or fragment or derivative thereof for the manufacture of a medicament for the treatment and/or prophylaxis of neurologic diseases, wherein the antibody or fragment or derivative thereof cross-blocks the binding of an antibody according to claim 13 with an affinity $[K_D]$ of 100 pM or less.

Another embodiment of the present invention is the use of an antibody or fragment or derivative thereof for the manufacture of a medicament for the treatment and/or prophylaxis of neurologic diseases, wherein the antibody or fragment or derivative thereof cross-blocks the binding by binding the same epitope as the antibody which it blocks.

Another embodiment of the present invention is the use of an antibody or fragment or derivative thereof for the manufacture of a medicament for the treatment and/or prophylaxis of neurologic diseases wherein the antibody or fragment or derivative thereof competes with the antibody or fragment or derivative thereof for binding to the extracellular domain of human CSF-1R (c-fms) of SEQ ID NO: 15.

An embodiment of the present invention provides the use of an antibody or fragment or derivative thereof for the manufacture of a medicament for the treatment and/or prophylaxis of neurologic diseases, which binds to the epitope of human CSF-1R.

Another embodiment of the present invention provides the use of an antibody or fragment or derivative thereof for the manufacture of a medicament for the treatment and/or prophylaxis of neurologic diseases which is an isolated DNA sequence encoding the heavy and/or light chain(s) of an antibody suitable for present invention.

As described herein, inhibitors of CSF-1R activity can be used in the treatment and/or prophylaxis of neurologic disease. For such use the agents will generally be administered in the form of a pharmaceutical composition. Also provided is a pharmaceutical composition comprising an inhibitor of CSF-1R activity in combination with a pharmaceutically acceptable diluent, excipient and/or carrier. A pharmaceutical composition of present invention also may additionally comprise other active ingredients.

The term 'treatment' includes either therapeutic and/or prophylactic therapy. When a reference is made herein to a method of treating and/or preventing a neurologic disease or condition using a particular inhibitor or combination of inhibitors, it is to be understood that such a reference is intended to include the use of that inhibitor or combination of inhibitors for the manufacture of a medicament for the treatment and/or prophylaxis of neurologic disease.

The composition will usually be supplied as part of a sterile, pharmaceutical composition that will normally include a pharmaceutically acceptable carrier. This composition may be in any suitable form (depending upon the desired method of administering it to a patient). The inhibitors of use in the invention are preferably administered to a subject orally or intrarectally but may also be administered by a variety of other routes such as transdermally, subcutaneously, intranasally, intravenously and intramuscularly. The most suitable route for administration in any given case will depend on the particular inhibitor, the subject, and the nature and severity of the disease and the physical condition of the subject.

The inhibitors of use in the invention may be administered in combination, e.g. simultaneously, sequentially or separately, with one or more other therapeutically active compounds, which may be for example an anti-neurologic therapy.

Pharmaceutical compositions maybe conveniently presented in unit dose forms containing a predetermined amount of an active agent of the invention per dose. Such a unit may contain for example but without limitation, 1000 mg/kg to 0.01 mg/kg for example 750 mg/kg to 0.1 mg/kg, such as 100 mg/kg to 1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art. In the case of oral solid preparations such as powders, capsules and tablets, carriers such as starches, sugars, microcrystalline cellulose, granulating agents, lubricants, binders, disintegrating agents, and the like may be included. Because of their ease of administration, tablets and capsules represent the most advantageous oral dosage unit form in which case solid pharmaceutical carriers are generally employed.

In addition to the common dosage forms set out above, active agents of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active agent, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active agent with the carrier, which constitutes one or more necessary ingredients. In general, the compositions are prepared by uniformly and intimately admixing the active agent with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the active agents of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms. The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets. Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollients in creams or ointments and ethanol or oleyl alcohol for lotions. Such carriers may be present as from about 1 percent up to about 98 percent of the composition. More usually they will form up to about 80 percent of the composition. As an illustration only, a cream or ointment is prepared by mixing sufficient quantities of hydrophilic material and water, containing from about 5-10 percent by weight of the compound, in sufficient quantities to produce a cream or ointment having the desired consistency. Pharmaceutical compositions adapted for transdermal administration may be presented as discrete patches intended to remain in intimate contact with the epidermis of the recipient for a prolonged period of time. For example, the active agent may be delivered from the patch by iontophoresis. For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base. Pharmaceutical compositions adapted for topical administration in the mouth include lozenges, pastilles and mouth washes. Pharmaceutical compositions adapted for topical administration to the eye include eye drops wherein the active agent is dissolved or suspended in a suitable carrier, especially an aqueous solvent. They also include topical ointments or creams as above. Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted capier(s) followed by chilling and shaping moulds. They may also be administered as enemas.

The dosage to be administered of an inhibitor of CSF-1R activity will vary according to the particular inhibitor, the type of neurologic disease, the subject, and the nature and severity of the disease and the physical condition of the subject, and the selected route of administration; the appropriate dosage can be readily determined by a person skilled in the art. For the treatment and/or prophylaxis of neurologic disease in humans and animals pharmaceutical compositions comprising antibodies can be administered to patients (e.g., human subjects) at therapeutically or prophylactically effective dosages (e.g. dosages which result in inhibition of neurologic disease and/or relief of neurologic disease symptoms) using any suitable route of administration, such as injection and other routes of administration known in the art for clinical products, such as antibody-based clinical products. The compositions may contain at least 0.05 percent by weight, for example 0.5 to 50 percent by weight such as 1 to 10 percent by weight, or more, by weight, of the inhibitor of the invention, depending on the method of administration. It will be recognized by one of skill in the art that the optimal quantity and spacing of individual dosages of an inhibitor of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

In one aspect, the pharmaceutical composition of the present invention comprises a CSF-1, IL-34 or CSF-1R nucleic acid, said nucleic acid being part of an expression vector that expresses a CSF1, IL-34 or CSF-1R polypeptide or chimeric protein thereof in a suitable host. In particular, such a nucleic acid has a promoter operably linked to the polypeptide coding region, said promoter being inducible or constitutive (and, optionally, tissue-specific).

One aspect of present invention provides a pharmaceutical composition for use in the treatment and/or prophylaxis of neurologic disease.

The present invention further provide a method for the treatment and/or prophylaxis of a human subject suffering from or at risk of developing a neurologic disease, which comprises administering to the subject a therapeutically effective amount of an inhibitor of CSF-1R activity. In an embodiment of the present invention the method for the treatment and/or prophylaxis of a human subject suffering from or at risk of developing a neurologic disease pertain administering to the subject a therapeutically effective amount of an inhibitor according to present invention, or a pharmaceutical composition according to present invention.

The present invention further provides a method for the treatment and/or prophylaxis of a human subject suffering from or at risk of developing a neurologic disease wherein the inhibitor of CSF-1R activity is administered in combination with one or more other therapeutically active compounds. Another aspect of the present invention provides a method in which the other therapeutically active compound is another anti-epileptic therapeutic agent.

The present invention provides an inhibitor of CSF-1R activity for use in the treatment and/or prophylaxis of neurologic diseases, the use of an inhibitor of CSF-1R activity for the manufacture of a medicament for the treatment and/or prophylaxis of neurologic diseases, a pharmaceutical composition comprising an inhibitor of CSF-1R activity for use in the treatment and/or prophylaxis of neurologic diseases or the method for the treatment and/or prophylaxis of a human subject suffering from or at risk of developing a neurologic disease, wherein the neurologic disease is selected from the group consisting of Alzheimer's disease, Amyotrophic lateral sclerosis (ALS), Angelman syndrome, Attention deficit hyperactivity disorder, Autism spectrum, Bipolar disorder, Brain damage, Brain injury, Brain tumor, Central pain syndrome, Cerebral atrophy, Chronic inflammatory demyelinating polyneuropathy (CIDP), Chronic pain, Complex regional pain syndrome, Creutzfeldt-Jakob disease, Dementia, Down syndrome, Dravet syndrome, Encephalitis, Essential tremor, Friedreich's ataxia, Fragile X syndrome, Fragile X-associated tremor/ataxia syndrome (FXTAS), Head injury, Headache, Herpes zoster, Huntington's disease, Hypoxia, Immune-Mediated encephalomyelitis, Infantile spasms, Intracranial hypertension, Lafora disease, Landau-Kleffner syndrome, Lennox-Gastaut syndrome, Leukodystrophy, Leukoencephalopathy with vanishing white matter, Lewy body dementia, Lissencephaly, Lyme disease—Neurological Sequelae, Megalencephaly, Meningitis, Microcephaly, Migraine, Mini-stroke (transient ischemic attack), Motor Neurone Disease—see amyotrophic lateral sclerosis, Multi-infarct dementia, Multiple sclerosis, Myoclonic Encephalopathy of infants, Myoclonus, Neurological manifestations of AIDS, Neurological sequelae of lupus, Neuronal ceroid lipofuscinosis, Neuropathy, Niemann-Pick disease, Ohtahara syndrome, Parkinson's disease, Paraneoplastic diseases, Primary Lateral Sclerosis, Prion diseases, Progressive multifocal leukoencephalopathy, Progressive Supranuclear Palsy, Rasmussen encephalitis, Restless legs syndrome, Rett syndrome, Stiff-person syndrome, Stroke, Transient ischemic attack, Traumatic brain injury, Tremor, Tuberous sclerosis, Unverricht-Lundborg disease, Uncinate epilepsy, West syndrome, Wilson's disease.

In embodiments of the present invention the neurologic disease is preferably selected from a group comprising Angelman syndrome, Attention deficit hyperactivity disorder, Autism spectrum, Brain injury, Brain tumor, Creutzfeldt-Jakob disease, Down syndrome, Dravet syndrome, Encephalitis, Fragile X syndrome, Fragile X-associated tremor/ataxia syndrome (FXTAS), Head injury, Herpes zoster, Hypoxia, Immune-Mediated encephalomyelitis, Infantile spasms, Lafora disease, Landau-Kleffner syndrome, Lennox-Gastaut syndrome, Leukodystrophy, Leukoencephalopathy with vanishing white matter, Lissencephaly, Lyme disease—Neurological Sequelae, Meningitis, Multiple sclerosis, Myoclonic Encephalopathy of infants, Myoclonus, Neurological sequelae of lupus, Ohtahara syndrome, Prion diseases, Rasmussen encephalitis, Rett syndrome, Traumatic brain injury, Tuberous sclerosis, Unverricht-Lundborg disease, Uncinate epilepsy or West syndrome.

In another embodiment of the present invention the neurologic disease is selected from the group comprising epilepsy, epileptogenesis, seizures and convulsions. In a further embodiment of the present invention, the type of epilepsy is selected from the group comprising generalized seizures, focal seizures and seizures of unknown origin. In another embodiment of the present invention the neurologic disease is temporal lobe epilepsy (TLE).

As a most preferred embodiment the anti-CSF-1R antibody as disclosed in WO15/028455 is incorporated herein by reference.

The invention will now be described with reference to the following examples, which are merely illustrative and should not in any way be construed as limiting the scope of the present invention.

CA019_969 Ab sequences:
CDR-L1,
(SEQ ID NO: 1)
LASEDIYDNLA;

CDRL2,
(SEQ ID NO: 2)
YASSLQD;

CDR-L3,
(SEQ ID NO: 3)
LQDSEYPWT;

CDR-H1,
(SEQ ID NO: 4)
GFSLTTYGMVG;

CDR-H2,
(SEQ ID NO: 5)
NIWWDDDKYYNPSLKN;

CDR-H3,
(SEQ ID NO: 6)
IGPIKYPTAPYRYFDF;

969 gL7 V-region:
(SEQ ID NO: 7)
DIQMTQSPSS LSASVGDRVT ITCLASEDIY DNLAWYQQKP
GKAPKLLIYY ASSLQDGVPS RFSGSGSGTD YTLTISSLQP
EDFATYYCLQ DSEYPWTFGG GTKVEIK;

969 gL7 V-region:
(SEQ ID NO: 8)
gacatacaga tgactcagtc ccctcaagc ctgagtgcca
gtgtgggaga cagggtgaca atcacctgtc tggcctccga
ggatatctac gataacctgg catggtatca gcagaaacct
ggaaaggctc ccaagctcct gatttattat gcctcctctc
tccaagacgg cgttccatct cggttcagcg gaagcggctc
cgggacggat tacacactga caattagctc tctgcaaccg
gaggattttg ctacttacta ctgcctgcaa gactccgaat
acccatggac cttcggtggt ggcaccaaag tggaaatcaa g;

969 gH2 V-region:
(SEQ ID NO: 9)
EVTLKESGPA LVKPTQTLTL TCTFSGFSLT TYGMGVGWIR
QPPGKALEWL ANIWWDDDKY YNPSLKNRLT ISKDTSKNQV
VLTMTNMDPV DTATYYCARI GPIKYPTAPY RYFDFWGQGT MVTVS;

969 gH2 V-region:
(SEQ ID NO: 10)
gaagtgacac tcaaggagtc tggacccgct ctggtgaaac
caacccaaac actcactttg acatgtactt ttagtggctt
ctcattgact acctatggaa tgggcgtggg atggatcaga
cagccacctg gcaaggctct ggaatggctg gccaacatct
ggtgggatga cgacaagtac tataaccgt ccctgaaaaa
ccggctgacc attagcaagg atacttctaa aaatcaagtg
gtgctgacca tgacaaatat ggatcccgtt gacaccgcaa
cctactactg cgcccgcatt ggtcccataa agtaccctac
ggcaccttac cgatatttcg acttttgggg ccaagggaca
atggttactg tctcg;

Amino acid sequence for CSF-1R:
(SEQ ID NO: 11)
MGPGVLLLLL VATAWHGQGI PVIEPSVPEL VVKPGATVTL
RCVGNGSVEW DGPPSPHWTL YSDGSSSILS TNNATFQNTG
TYRCTEPGDP LGGSAAIHLY VKDPARPWNV LAQEVVVFED
QDALLPCLLT DPVLEAGVSL VRVRGRPLMR HTNYSFSPWH
GFTIHRAKFI QSQDYQCSAL MGGRKVMSIS IRLKVQKVIP
GPPALTLVPA ELVRIRGEAA QIVCSASSVD VNFDVFLQHN
NTKLAIPQQS DFHNNRYQKV LTLNLDQVDF QHAGNYSCVA
SNVQGKHSTS MFFRVVESAY LNLSSEQNLI QEVTVGEGLN
LKVMVEAYPG LQGFNWTYLG PFSDHQPEPK LANATTKDTY
RHTFTLSLPR LKPSEAGRYS FLARNPGGWR ALTFELTLRY
PPEVSVIWTF INGSGTLLCA ASGYPQPNVT WLQCSGHTDR
CDEAQVLQVW DDPYPEVLSQ EPFHKVTVQS LLTVETLEHN
QTYECRAHNS VGSGSWAFIP ISAGAHTHPP DEFLFTPVVV
ACMSIMALLL LLLLLLLYKY KQKPKYQVRW KIIESYEGNS
YTFIDPTQLP YNEKWEFPRN NLQFGKTLGA GAFGKVVEAT
AFGLGKEDAV LKVAVKMLKS TAHADEKEAL MSELKIMSHL
GQHENIVNLL GACTHGGPVL VITEYCCYGD LLNFLRRKAE
AMLGPSLSPG QDPEGGVDYK NIHLEKKYVR RDSGFSSQGV
DTYVEMRPVS TSSNDSFSEQ DLDKEDGRPL ELRDLLHFSS
QVAQGMAFLA SKNCIHRDVA ARNVLLTNGH VAKIGDFGLA
RDIMNDSNYI VKGNARLPVK WMAPESIFDC VYTVQSDVWS
YGILLWEIFS LGLNPYPGIL VNSKFYKLVK DGYQMAQPAF
APKNIYSIMQ ACWALEPTHR PTFQQICSFL QEQAQEDRRE
RDYTNLPSSS RSGGSGSSSS ELEEESSSEH LTCCEQGDIA
QPLLQPNNYQ FC;

Amino acid sequence for CSF-1R:
(SEQ ID NO: 12)
IPVIEPSVPELVVKPGATVTLRCVGNGSVEWDGPPSPHWTLYSDGSSSIL
STNNATFQNTGTYRCTEPGDPLGGSAAIHLYVKDPARPWNVLAQEVVVFE
DQDALLPCLLTDPVLEAGVSLVRVRGRPLMRHTNYSFSPWHGFTIHRAKF
IQSQDYQCSALMGGRKVMSISIRLKVQKVIPGPPALTLVPAELVRIRGEA
AQIVCSASSVDVNFDVFLQHNNTKLAIPQQSDFHNNRYQKVLTLNLDQVD
FQHAGNYSCVASNVQGKHSTSMFFRVV;

Amino acid sequence for CSF-1R:
(SEQ ID NO: 13)
MRHTNYSFSPWHGFTIHRAKFIQSQDYQCSALMGGRKVMSISIRLKVQK;

Amino acid sequence for CSF-1R (SNP V32G, A245S, H247P, V279M, position underlined):
(SEQ ID NO: 14)
IPVIEPSVPELV̲VKPGATVTLRCVGNGSVEWDGPPSPHWTLYSDGSSSIL
STNNATFQNTGTYRCTEPGDPLGGSAAIHLYVKDPARPWNVLAQEVVVFE
DQDALLPCLLTDPVLEAGVSLVRVRGRPLMRHTNYSFSPWHGFTIHRAKF
IQSQDYQCSALMGGRKVMSISIRLKVQKVIPGPPALTLVPAELVRIRGEA -continued

AQIVCSASSVDVNFDVFLQHNNTKLAIHQQSDFHNNRYQKVLTLNLDQVD

FQHAGNYSCVASNVQGKHSTSMFFRVVESAYLNLSSEQNLIQEVTVGEGL

NLKVMVEAYPGLQGFNWTYLGPFSDHQPEPKLANATTKDTYRHTFTLSLP

RLKPSEAGRYSFLARNPGGWRALTFELTLRYPPEVSVIWTFINGSGTLLC

AASGYPQPNVTWLQCSGHTDRCDEAQVLQVWDDPYPEVLSQEPFHKVTVQ

SLLTVETLEHNQTYECRAHNSVGSGSWAFIPISAGAHTHPPDE;

SEQ ID NO: 15:
MGPGVLLLLL VATAWHGQGI PVIEPSVPEL VVKPGATVTL

RCVGNGSVEW DGPPSPHWTL YSDGSSSILS TNNATFQNTG

TYRCTEPGDP LGGSAAIHLY VKDPARPWNV LAQEVVVFED

QDALLPCLLT DPVLEAGVSL VRVRGRPLMR HTNYSFSPWH

GETIHRAKFI QSQDYQCSAL MGGRKVMSIS IRLKVQKVIP

GPPALTLVPA ELVRIRGEAA QIVCSASSVD VNFDVFLQHN

NTKLAIPQQS DFHNNRYQKV LTLNLDQVDF QHAGNYSCVA

SNVQGKHSTS MFFRVVESAY LNLSSEQNLI QEVTVGEGLN

LKVMVEAYPG LQGFNWTYLG PFSDHQPEPK LANATTKDTY

RHTFTLSLPR LKPSEAGRYS FLARNPGGWR ALTFELTLRY

PPEVSVIWTF INGSGTLLCA ASGYPQPNVT WLQCSGHTDR

CDEAQVLQVW DDPYPEVLSQ EPFHKVTVQS LLTVETLEHN

QTYECRAHNS VGSGSWAFIP ISAGAHTHPP DE.

FIGURES

Figure 3:
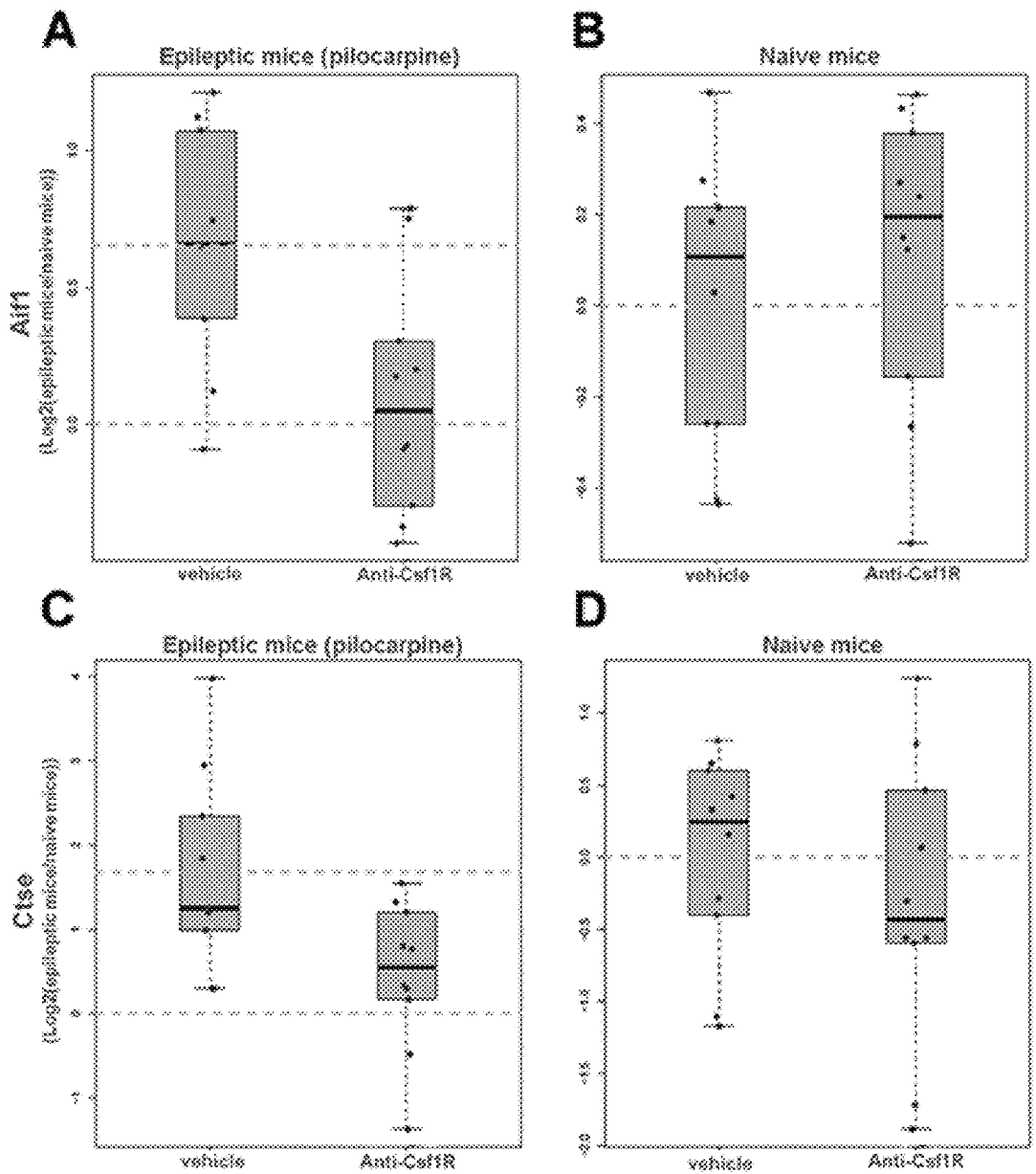
Figure 3:
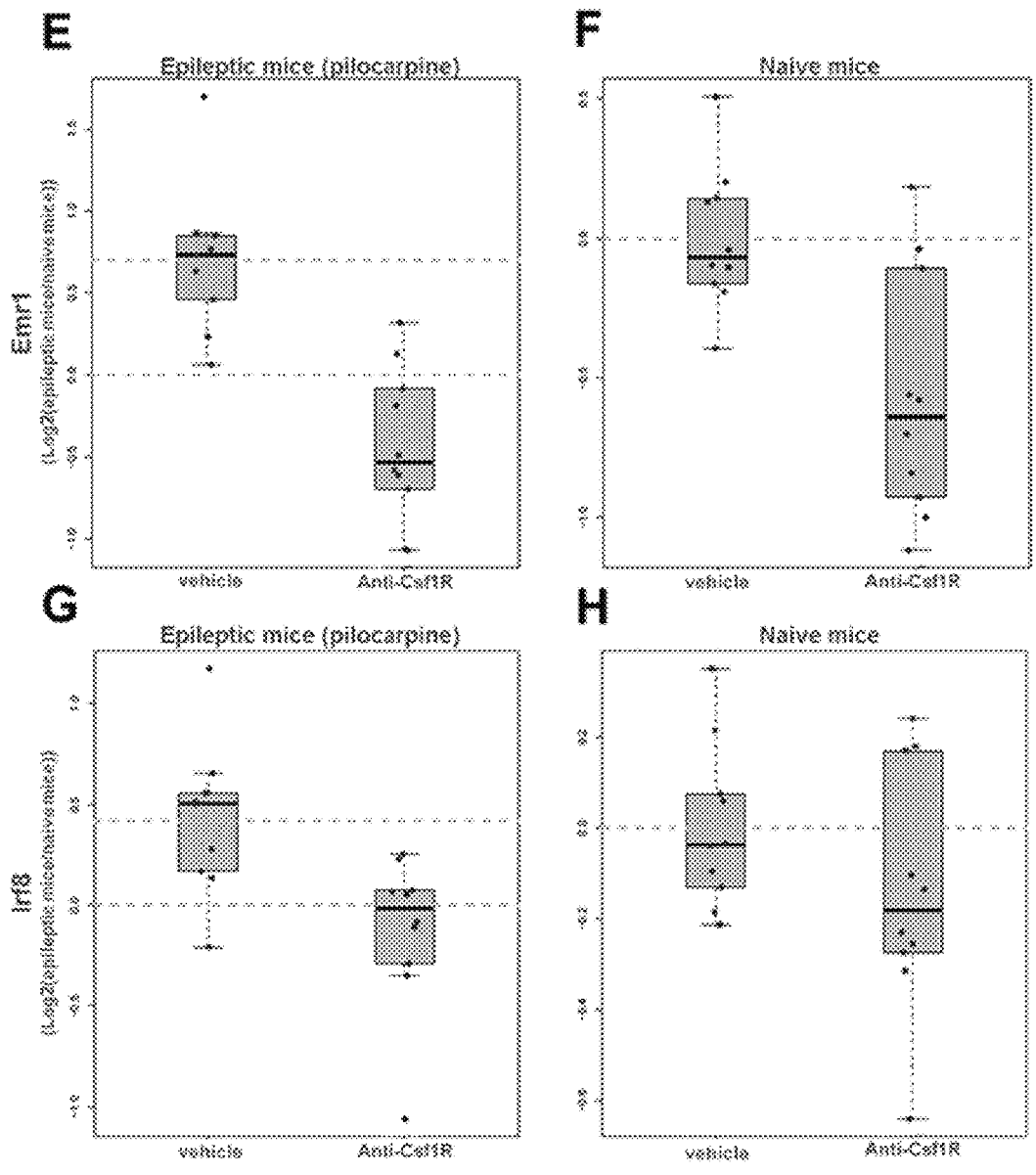

FIG. 3 shows CSF-1R transcriptional target engagement in mice after treatment (s.c.) with anti-CSF-1R antibody. The expression of four transcriptional target genes of CSF-1R, e.g. Aif1 (panels A,B), Ctse (panel C,D), Emr1 (panel E,F) and Irf8 (panel G,H), was measured by qPCR in hippocampi of epileptic mice (left panels) and naïve animals (right panels) after s.c. injections of anti-CSF-1R antibody or control IgG as a negative control.

Figure 4:
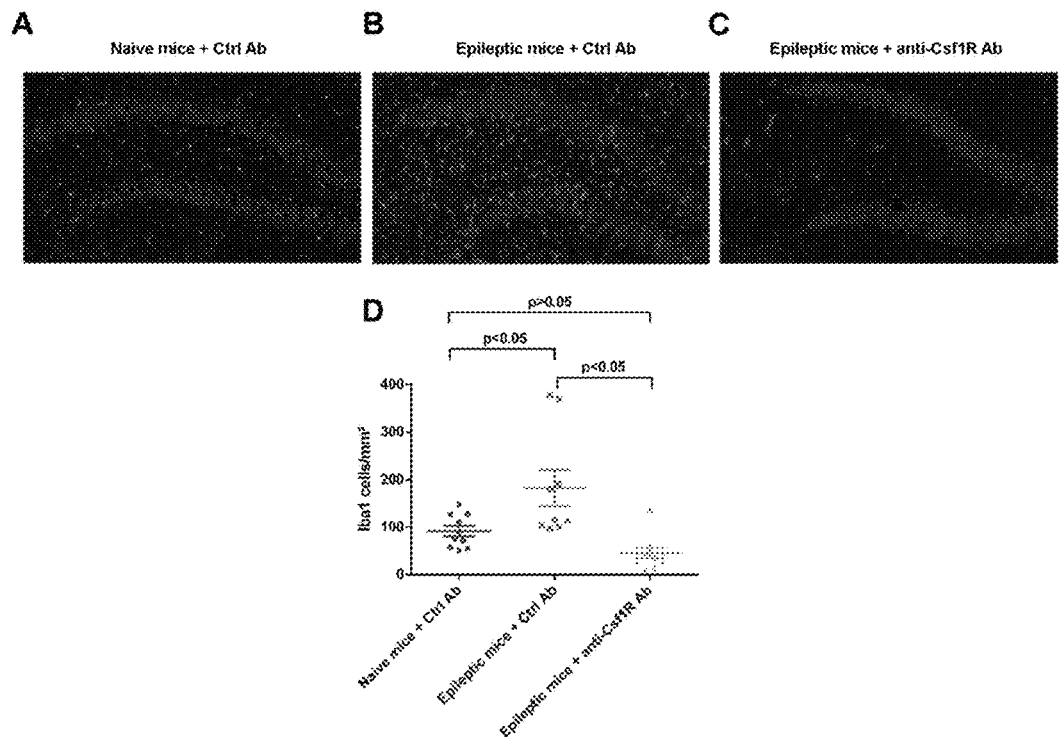

FIG. 4 shows the results of immunohistochemistry experiments performed on mouse brain slices (dentate gyrus of the hippocampus) after treatment (s.c.) with anti-CSF-1R antibody. Iba1 protein, which is a marker of activated microglia was labelled in red, while cell nuclei were stained in blue by DAPI (panels A-C). The density of Iba1-expressing microglial cells per mm$^2$ was quantified in panel D.

Figure 5:
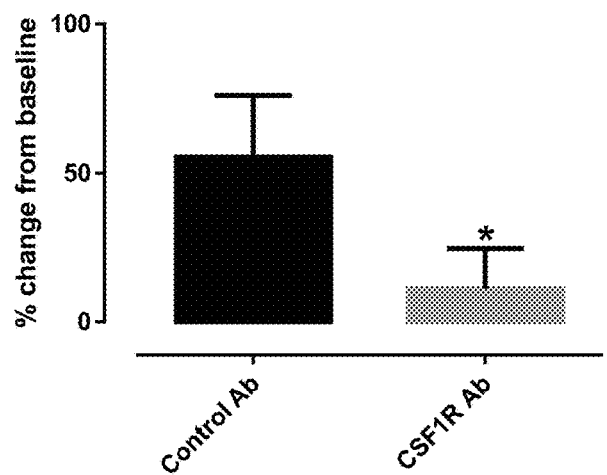
Figure 6:
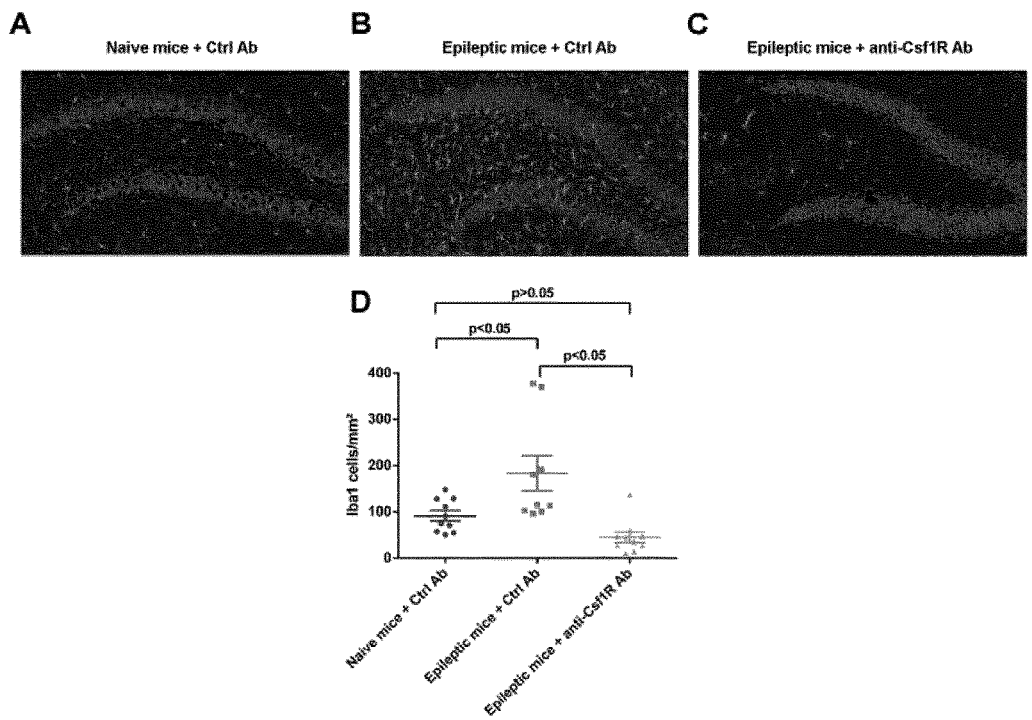
Figure 7:
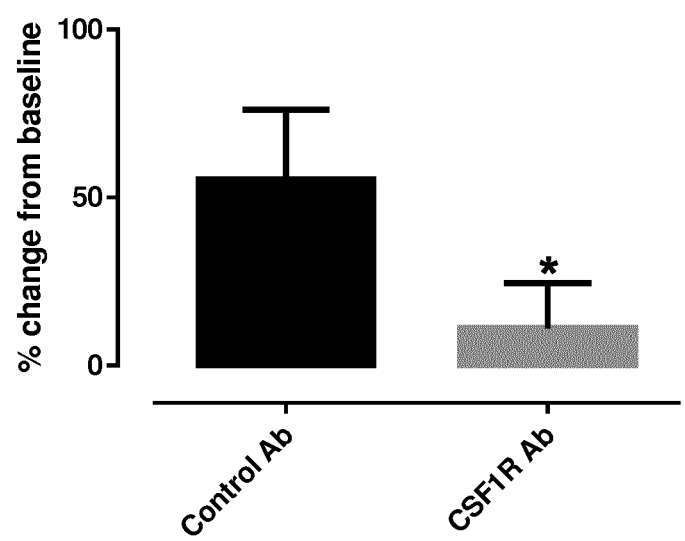

FIG. 5 shows the protective effect of an anti-CSF1R antibody on the frequency of epileptic seizures in a pilocarpine mouse model.

EXAMPLE 1 ISOLATION OF AN ANTI-MOUSE CSF-1R ANTIBODY 2 rabbits received 5 immunisations with cells transiently expressing residues 1-512 of mouse CSF-1R (Uniprot Entry p09581). Antibody response was monitored in an ELISA using Nunc Maxisorp plates coated with 2 µg/ml mouse CSF-1R-Rabbit Fc. Sera titres out to 1:100,000 dilution were observed with both rabbits. Binding of sera to M-NFS-60 cells (Metcalf et al., 1970) was also determined by FACS. Median FL1 was plotted against antibody dilution. Binding out to a dilution of 1:10,000 was observed.

Using the CSF-1-dependent M-NFS-60 cell line (Metcalf et al., 1970), it was shown that sera from both rabbits could block CSF-1-dependent cell survival out to a dilution of 1:100 (data not shown).

One hundred 96-well plates were seeded with 1000-5000 rabbit PBMCs per well and grown for 1 week at 37 C in the presence of EL4-B5 mouse thymoma cells and rabbit T cell conditioned media (TSN). Antibody-containing supernatants were then screened in an FMAT assay using M-NFS-60 cells and anti-rabbit Fc-specific Cy5 conjugate. 678 CSF-1R-binders were identified. From these, approximately 3% blocked CSF-1-dependent M-NFS-60 proliferation in a cell assay. Binders were also screened in an ELISA using plates coated with 2 µg/ml CSF-1R-rabbit Fc and binding revealed with an anti-rabbit F(ab')2-HRP conjugate. Binders were also screened in an ELISA-based solid-phase blocking assay. For this assay, Nunc Maxisorp 384-well plates were coated with 0.5 µg/ml CSF-1R-rabbit Fc and subsequently blocked in PBS/0.1% Tween-20/1% PEG20000. Plates were washed before culture supernatant was then added to the plates and incubated for >1 hour at room temperature. CSF-1 was then added into the supernatant at a final concentration of 10 ng/ml and incubated for a further 1 hour at room temperature. Plates were washed and then incubated with 0.5 µg/ml biotinylated goat anti-mouse CSF-1 antibody (R&D systems). CSF-1 binding to receptor was revealed using streptavidin-HRP. Eight wells were selected for progression. All demonstrated binding to cells and protein and blocked in the M-NFS-60 assay and in the ELISA.

A fluorescence-based method was used to identify the antigen-specific B cells from a positive well. Immunoglobulin-secreting B cells from a positive well were mixed with streptavidin beads coated with biotinylated mouse CSF-1R-rabbit Fc and a goat F(ab')2 anti-rabbit F(ab')2 fragment-specific FITC conjugate (Jackson ImmunoResearch). After incubation at 37 C for 1 hour, antibody secreted from antigen-specific B cells was captured on beads in the vicinity of that B cell. The presence of the FITC conjugate resulted in the labelling of antibody-coated beads and the formation of fluorescent foci around the antigen-specific B cells. These individual B cells, identified using a fluorescent microscope, were then picked with a micromanipulator and deposited into a PCR tube. Antibody variable region genes were recovered from single cells by reverse transcription (RT)-PCR. Rabbit V-regions were then expressed as human IgG4 chimeric antibodies or Fabs in a CHO transient expression system. 4 out of 8 wells produced recombinant anti-CSF-1R antibodies. Neutralisation activity with the recombinant antibodies was then confirmed in the M-NFS-60 assay. BIAcore was also performed using the Fab molecules to determine affinity for CSF-1R rabbit Fc (Table 1). Based on neutralisation activity and affinity, Ab535 was selected as the anti-mouse CSF-1R reagent. This antibody was subsequently murinised, expressed in a mammalian system as full length murine IgG1 and purified.

BIAcore Method

Antibodies were tested for their ability to bind CSF-1R in a BIAcore assay by measurement of binding kinetics to a purified recombinant CSF-1R/Fc fusion protein.

The assay format was capture of the anti-CSF-1R antibodies by immobilised anti-human IgG, F(ab')$_2$, then a titration of hCSF-1R/Fc over the captured surface. BIA (Biamolecular Interaction Analysis) was performed using a BIAcore 3000 (GE Healthcare Bio-Sciences AB). All experiments were performed at 25° C. Affinipure F(ab')$_2$ fragment goat anti-human IgG, F(ab')$_2$ fragment specific (Jackson ImmunoResearch) was immobilised on a CM5 Sensor Chip (GE Healthcare Bio-Sciences AB) via amine coupling chemistry to a level of ~6000 response units (RU). HBS-EP buffer (10 mM HEPES pH 7.4, 0.15 M NaCl, 3 mM EDTA, 0.005% Surfactant P20, GE Healthcare Bio-Sciences AB) was used as the running buffer with a flow rate of 10 µl/min. An injection of an anti-CSF-1R antibody was performed to give a capture level of approximately 100 RU on the immobilised anti-human IgG, F(ab')$_2$.

Recombinant human CSF-1R/Fc was titrated (R&D Systems), by doubling dilution, from 2.5 nM to 78 pM over the captured anti-CSF-1R antibody at a flow rate of 30 µl/min for 3 min followed by a 8 min dissociation phase. These sensorgrams were used to generate the association rate. The surface was regenerated at a flow rate of 10 µl/min by two sequential 10 µl injections of 40 mM HCl followed by a 5 µl injection of 10 mM NaOH. Double referenced background subtracted binding curves were analysed using the BIAevaluation software (version 4.1) following standard procedures. Kinetic parameters were determined from the fitting algorithm.

The results for Ab553 are shown in Table 1.

TABLE 1

| ANTIBODY REF: | On Rate ka (M$^{-1}$s$^{-1}$) | Off Rate kd (s$^{-1}$) | Affinity Constant K$_D$ |
|---|---|---|---|
| Ab 535 | 8.05 ± 0.01e6 | 1.21 ± 0.15e−5 | 1.50 pM |

EXAMPLE 2 IN VITRO ANALYSIS OF AB535

Ab535 Blocks Binding of Murine CSF-1 to CSF-1 Receptor-Positive Cell Lines In Vitro The capacity of receptor-bound Ab535 to prevent CSF-1 from binding to CSF-1R was investigated. A murine CSF-1R-positive cell line, M-NFS-60, was used in assay in which cells were pre-incubated with Ab535 or a control antibody prior to exposure to CSF-1. Receptor-bound CSF-1 was then detected using a fluorescently-labelled antibody and flow cytometry. An Ab535-dependent decrease in cell fluorescence intensity was interpreted as indicating a capacity of receptor-bound Ab535 to prevent the binding of CSF-1 to CSF-1R.

M-NFS-60 cells (LGC Promochem, Teddington, UK) were maintained in suspension in basal RPMI medium (Invitrogen) supplemented with 10% fetal calf serum (PAA), Hepes (Invitrogen, 10 mM final concentration), Sodium Pyruvate (Invitrogen, 1 mM final concentration) Glucose (Sigma-Aldrich, 4.5 g/l final concentration), Sodium bicarbonate (Sigma-Aldrich, 1.5% final concentration), beta-mercaptoethanol (Sigma-Aldrich, 0.05 mM final concentration), recombinant murine CSF-1 (Preprotech, 3.3 ng/ml final concentration).

M-NFS-60 cells were prepared in flow buffer (PBS (Invitrogen) supplemented with 0.2% BSA (Sigma-Aldrich), 0.09% sodium azide (Sigma-Aldrich)) at a concentration of 1×10E6 cells/ml. Serial dilutions of Ab535 or a murine IgG1 isotype control antibody were prepared in flow buffer and added to 100 µl aliquots of cells to achieve final concentrations of 20, 5, 1.25, 0.32, 0.08 µg/ml in 200 µl volume and were incubated on ice for 1 hour. Thereafter, cells were washed twice in flow buffer, incubated with 0.5 µg/ml recombinant murine CSF-1 for 30 mins on ice and washed twice in flow buffer. To detect receptor-bound CSF-1, cells were incubated with a biotinylated anti-murine CSF-1 antibody (R&D Systems, 5 µg/ml) for 30 minutes on ice, washed twice in flow buffer and bound antibody labelled by incubation with Alexafluor 488-conjugated straptavidin (Invitrogen, 1:200 dilution) on ice for 15 minutes prior to a final washing step and resuspension of cells in 500 µl flow buffer. Cells were assessed for fluorescence by flow cytometry using a FACSCaliber flow cytometer (Becton Dickinson) and data were analysed using WinMDI software.

Figure 1:
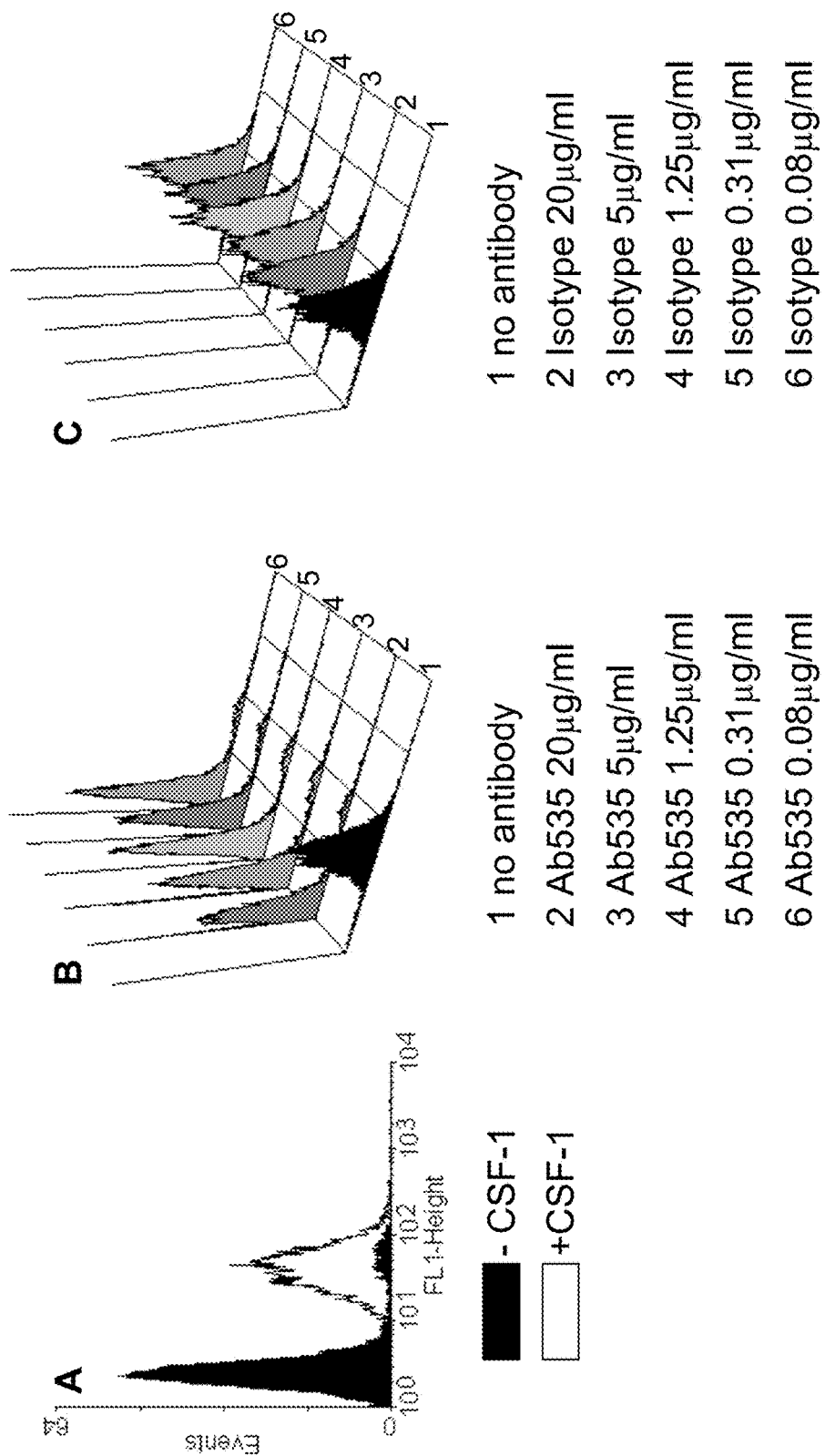
FIG. 1 shows flow cytometry data confirming that receptor-bound CSF-1 on M-NFS-60 cells was detectable by this method.

Analysis of flow cytometry data confirmed that receptor-bound CSF-1 on M-NFS-60 cells was detectable by this method (FIG. 1a). Incubation of cells with Ab535 at any of the concentrations used, prior to addition of CSF-1 prevented binding of CSF-1 to CSF-1R as (FIG. 1b). Incubation of cells with an isotype control antibody at any of the concentrations used had no effect on CSF-1 binding and detection (FIG. 1c).

Binding of Ab535 to CSF-1R does not Substitute for CSF-1 in the Proliferation and Survival of a CSF-1 Dependent Cell Line In Vitro The capacity of Ab535 to substitute for CSF-1 in supporting the survival and proliferation of CSF-1-dependent cells was investigated using M-NFS-60 cells in a cell proliferation assay that included exposing cells to Ab535 free in solution and immobilised on plastic.

To assess the capacity of immobilised Ab535 to support CSF-1-dependent cells, wells of a 96-well round-bottomed tissue culture plate were pre-coated with Ab535 or an irrelevant isotype control antibody for 24 hours prior to initiating the cell proliferation assay by addition of 50 µl per well of a solution containing 10 µg/ml or 1 µg/ml of antibody in PBS and incubation at 4° C. Wells were aspirated and unbound antibody removed by washing each well twice with 100 µl PBS.

Proliferating M-NFS-60 cells, maintained as described above, were seeded into 96-well round-bottomed tissue culture plates at a density of 10,000 cells per well in 50 µl of growth medium without CSF-1. A further 50 µl growth medium, supplemented with either recombinant murine CSF-1, Ab535 or with no supplements, was added to appropriate wells. Plates were incubated for 72 hours and cell number was determined using a CellTiter Glo kit according to the manufacturer's instructions (Promega) to generate a measurable luminescent readout proportional to levels of ATP and hence to cell number, for each of the conditions tested. All conditions were performed in triplicate.

Figure 2:
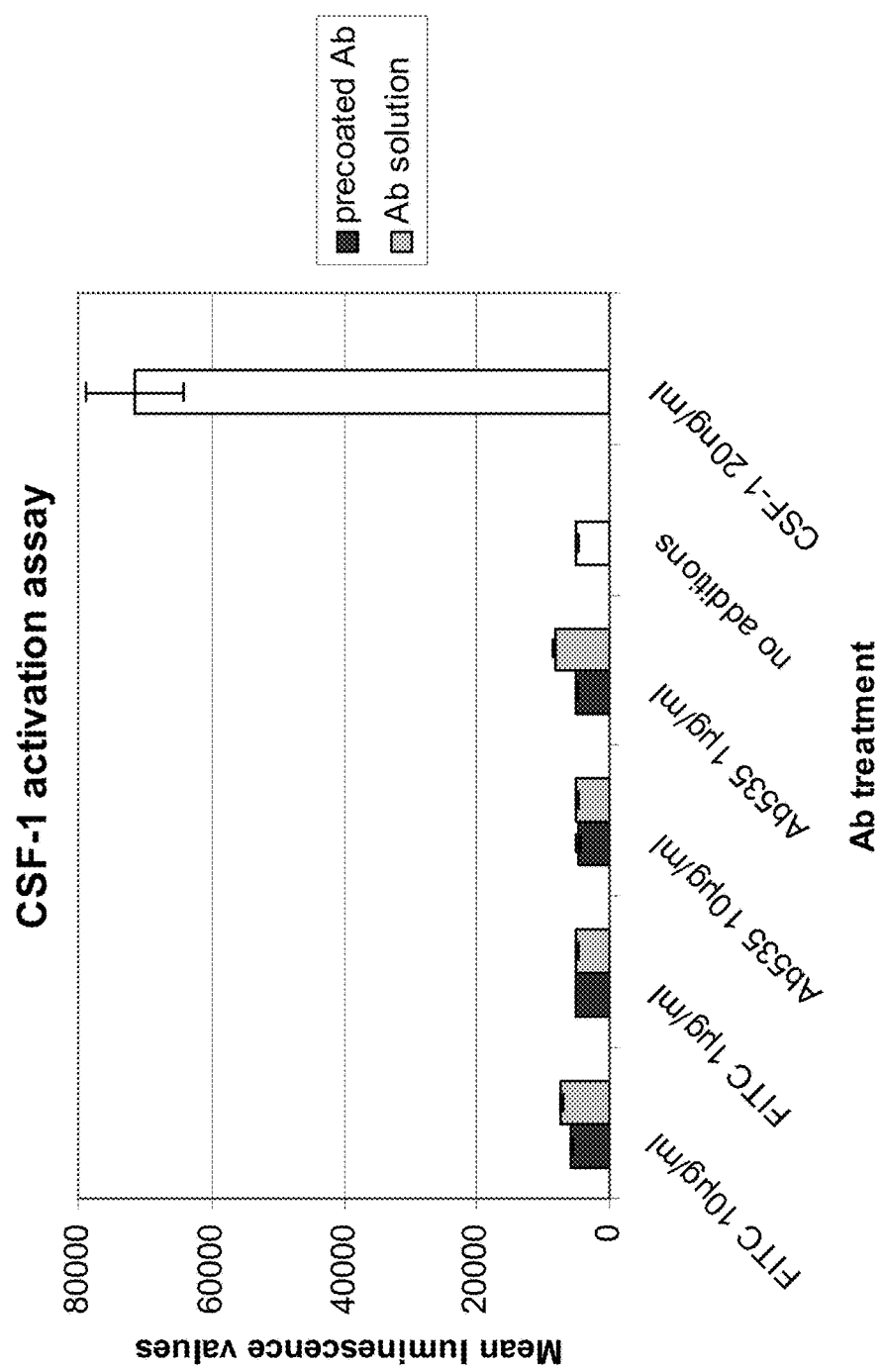
FIG. 2 shows Ab535, either immobilised on the surface of the tissue culture well, or free in solution, did not support the proliferation of M-NFS-60 cells in the absence of CSF-1 at the concentrations used.

Analysis of the data confirmed that M-NFS-60 are dependent on CSF-1 for proliferation, as reflected by the significantly higher cell number in wells supplemented with CSF-1 compared with those maintained in growth medium without CSF-1. Furthermore, Ab535, either immobilised on the surface of the tissue culture well, or free in solution, did not support the proliferation of M-NFS-60 cells in the absence of CSF-1 at the concentrations used (FIG. 2).

EXAMPLE 3: PILOCARPINE MOUSE MODEL OF TEMPORAL LOBE EPILEPSY

The pilocarpine model of temporal lobe epilepsy and epileptogenesis was performed as described by Mazzuferi et al., 2012. Naïve or epileptic mice (n=8-10) 19 weeks after induction of temporal lobe epilepsy by pilocarpine where administered 100 mg/kg (s.c.) anti-CSF-1R (Ab535) or vehicle on day 1 and 4 of experiment. On day 8, animals were sacrificed and their brains were removed from the skull.

Pilocarpine-induced temporal lobe epilepsy is associated with symmetrical changes in both brain hemispheres (Mazzuferi et al., 2012). The hippocampus was rapidly dissected form the right-side hemisphere and frozen at −80° C. to perform RNA extraction an qRT-PCR. The left-side hemisphere was fixed by immersion in 4% PFA in order to perform histological studies (immunohistochemistry).

In order to show molecular consequences of receptor blocking by the antibody, downstream transcriptional target genes of CSF-1R were identified using Thomson-Reuters Metabase (http://lsresearch.thomsonreuters.com/pages/solutions/10/metabase), a manually-curated database of biological pathways and gene regulation. Among the target CSF-1R genes Aif1, Irf8, Ctse1 and Emr1 genes were selected, because they are known to be expressed in the hippocampus. Their expression was measured and compared by qRT-PCR.

One of the above mentioned target genes of CSF-1R, Aif1, is coding Iba1 protein, which a widely established marker of microglia activation. The expression of Iba1 is consistently increased in microglial cells found in human epilepsy and in mouse models of epilepsy, such as the pilocarpine model (Vezzani et al., 2013). Therefore we performed immunohistochemical assessment of its expression in the hippocampus of pilocarpine epileptic mice treated with anti-CSF-1R antibody. Specific antibodies recognizing Iba1 (microglia marker) and DAPI (nuclear marker) were used, and the number of Iba1-positive cells was quantified (cells/mm$^2$) in the dentate gyrus of the hippocampus after image acquisition with 40× lens (Nano-Zoomer).

Results

The expression of four transcriptional target genes of CSF-1R, e.g. Aif1 (FIG. 5 panels A,B), Ctse (FIG. 3 panel C,D), Emr1 (FIG. 3 panel E,F) and Irf8 (FIG. 3 panel G,H), was measured by qPCR in hippocampi of epileptic mice (left panels) and naïve animals (right panels) after s.c. injections of anti-CSF-1R antibody or control IgG as a negative control.

In pilocarpine mice, anti-CSF-1R antibody treatment (s.c.) significantly decreased the expression of all 4 selected target genes (Aif1, Ctse, Emr1 and Irf8) compared to control (FIG. 3—panels A, C, E and G). This demonstrates that CSF-1R is efficiently inhibited in the hippocampus of epileptic mice treated with the anti-CSF-1R antibody.

The expression of Aif1, Ctse and Irf8 genes in naïve animals is not affected by anti-CSF-1R antibody (FIG. 3—panels B, D and H). This suggests that the disease state (epilepsy) is required for the anti-CSF-1R to have its effect in brain. However, Emr1 expression is also affected in naïve mice (FIG. 1—panel F), suggesting that some target genes of CSF-1R may depend on disease background while others not.

In epileptic mice, the anti-CSF-1R is restoring, at least partially, the expression levels of those 4 genes to the expression levels observed in naïve animals (panels A, C, E, and G), indicating target engagement in the brain of mice with epilepsy. In naïve animals, this effect can only be seen on Irf8 target genes (panel F), but not with the 3 other target genes (panels B, D and H), indicating a different target engagement of anti-CSF-1R exposure in naïve animals compared to pilocarpine-induced epileptic animals.

EXAMPLE 4: IMMUNOHISTOCHEMISTRY EXPERIMENTS PERFORMED ON MOUSE BRAIN SLICES

The observations described in example 3 based on gene expression data were confirmed by brain histology. FIG. 4 shows immunohistochemistry results performed on mouse brain slices (dentate gyrus of the hippocampus) after treatment (s.c.) with anti-CSF-1R antibody for Iba1 marker (in red), which is a marker of activated microglial cells; cell nuclei were stained in blue by DAPI. The density of Iba1-expressing microglial cells per mm$^2$ was quantified in panel D.

Iba1 protein is coded by Aif1 gene mentioned in example 3, a direct down-stream target gene of CSF-1R. As clearly shown (FIG. 4—panel B and quantification in panel D) there is a strong increase in microglia activation and staining for Iba1 positive cells in epileptic pilocarpine mice, when compared to naïve mice (FIG. 4—panel A and quantification in panel D). Injections (s.c.) with the anti-CSF-1R antibody produced a robust decrease in Iba1-positive cells in the epileptic animals (FIG. 4—panel C), which is consistent with a decrease in microglial activity. Hence, treatment with anti-CSF-1R antibody induced normalization of Iba1 staining (FIG. 4—panel C and quantification in panel D) to the control level.

EXAMPLE 5: MPTP MOUSE MODEL OF PARKINSON'S DISEASE

The selective acute degeneration of dopaminergic cells, which is a hallmark of Parkinson's disease, can be induced, e.g. in mice, by the toxins such as 1-methyl-4-phenyl-1,2,3,6-tetrahydropyridine (MPTP). After injection of MPTP dopaminergic cells degenerate over a period of a few days and this is accompanied by the activation of the microglia (Depboylu et al., 2012).

Two groups of naïve mice (n=8-10) were administered 100 mg/kg (s.c.) anti-CSF-1R (Ab535) or vehicle on day 1 and 4 of experiment. On day 8 both groups of mice are injected with MPTP (12.5 mg/kg; s.c). Systemic injection of MPTP rapidly induces symmetrical changes in both brain hemispheres therefore the mice were sacrificed 10-12 hrs after the toxin injection. The striatum was rapidly dissected form the right-side hemisphere and frozen at −80° C. to perform RNA extraction a qRT-PCR. The left-side hemisphere was fixed by immersion in 4% PFA in order to perform histological studies (immunohistochemistry).

In order to show molecular consequences of receptor blocking by anti-CSF-1R antibody the expression of the downstream transcriptional target genes Aif1, Irf8, Ctse1 and Emr1 were measured and compared by qRT-PCR. Iba1, a marker of activated microglial cells and cell nuclei (DAPI) were stained selective antibodies. The density of Iba1-expressing microglial cells per mm$^2$ was quantified in the striatum.

EXAMPLE 6: TESTING OF COMPOUNDS INTO THE ALPHA-SYNUCLEIN PRE-FORMED FIBRILS (PFFS) MICE MODEL IN PARKINSON'S DISEASE

Purified recombinant mice wild-type alpha-synuclein PFFs are centrifuged at high speed and the supernatant is collected. PFFs are assembled in micro-centrifuges tubes and shaken for 5 days (1,000 RPM). Aliquots are frozen on dry ice and stored at −80° C. PFFs are thawed at room temperature and sonicated. Concentration of the suspension before use is 2.5 µg/µl of protein in PBS. Subsequently, 10-week old male and/or female mice C57Bl/6J are anesthetized with ketamine/medetomidine and PFFs are injected into the right striatum at the following coordinates AP +0.2 mm, ML −2.0 mm, DV −3.0 mm (total volume of 2 µL at 0.1 µL/min). Anti-CSF-1R antibody (Ab 535; 100 mg/kg; s.c.) is administered once per week for one months starting the day after the PFFs injection. After this time the animals are assessed in a range of behavioral tests such as rotarod, beam test, wire-hanging test and gait analysis. After the behavioral testing the animals are sacrificed and their brains are removed. The right hemisphere is fixed by immersion in 4% PFA in order to perform histological studies (immunohistochemistry).

In order to show molecular consequences of receptor blocking by anti-CSF-1R antibody the expression of Iba1 microglia protein is measured by quantitative immunohistochemistry (as in Example 4). Finally, the distribution across the brain of pS129 alpha-synuclein, a measure of total alpha-synuclein, count of dopaminergic neurons in the striatum and substantia nigra is also performed.

EXAMPLE 7: PROTECTIVE EFFECT OF AN ANTI-CSF1R ANTIBODY ON SEIZURE FREQUENCY IN A PILOCARPINE MOUSE MODEL

A group of pilocarpine epileptic mice (prepared as described in the methods) underwent continuous monitoring to confirm that they display spontaneous recurrent seizures before entering into the efficacy study. The seizure monitoring was performed with a proprietary system (UCB Pharma) using simultaneous recording of locomotor activity with 3D accelerometer and video cameras. This system allows automated detection of behavioural seizures by analysis of the accelerometer signal. All behavioral seizures identified by the detection algorithm were then scored by experienced technical personnel during careful review of corresponding video clips. After confirming the presence of spontaneous recurrent seizures the mice (n=64) underwent a 14-day continuous monitoring with the same system to establish their baseline seizure frequency before starting the treatment. Subsequently, the mice (n=32 per group) were with treated with either control IgG or Anti-Csf1R antibodies (100 mg/kg), twice per week (4 injections total) during another 14 days of continuous seizure monitoring. Then the percent change in seizure frequency was calculated according to this formula:

$$\% \text{ change in seizure frequency} = (\text{seizure frequency during treatment}/\text{seizure frequency during baseline}) \times 100$$

Injection with the control IgG antibody led to an increase in seizure frequency vs. baseline, while such an increase was not observed after treatment with Anti-Csf1R antibody. Consequently, there was a statistically significant difference in seizure frequencies during the treatment phase when comparing control and active antibody groups (FIG. 5).

---

The invention claimed is:

1. A method for the treatment of a human subject suffering from or at risk of neurologic disease selected from the group consisting of epilepsy, epileptogenesis, seizures and convulsions comprising administering to the human subject having epilepsy, epileptogenesis, seizures or convulsions a therapeutically effective amount of an antibody that inhibits colony-stimulating factor 1 receptor (CSF-1R) activity, or a pharmaceutical composition thereof, said antibody comprising a heavy chain and a light chain, wherein the variable domain of the heavy chain comprises SEQ ID NO:4 for complementarity determining region (CDR) H1, SEQ ID NO:5 for CDR H2 and SEQ ID NO:6 for CDR H3 and the variable domain of the light chain comprises SEQ ID NO:1 for CDR LE SEQ ID NO:2 for CDR L2 and SEQ ID NO:3 for CDR L3.

2. The method according to claim 1, wherein the antibody is administered in combination with one or more anti-epileptic drug.

3. The method according to claim 1, wherein the neurologic disease is convulsions.

4. The method according to claim 1, wherein the neurologic disease is epilepsy.

5. The method according to claim 4, wherein the type of epilepsy is selected from the group consisting of generalized seizures, focal seizures and seizures of unknown origin.

6. The method according to claim 1, wherein the neurologic disease is epileptogenesis.

7. The method according to claim 1, wherein the neurologic disease is seizures.

8. The method according to claim 1, wherein said antibody comprises a heavy chain comprising SEQ ID NO:9 and a light chain comprising SEQ ID NO:7.

* * * * *

UNITED STATES PATENT AND TRADEMARK OFFICE
CERTIFICATE OF CORRECTION

Page 1 of 1

PATENT NO. : 10,316,097 B2
APPLICATION NO. : 15/577035
DATED : June 11, 2019
INVENTOR(S) : Patrice Marie Charles Godard et al.

It is certified that error appears in the above-identified patent and that said Letters Patent is hereby corrected as shown below:

In the Specification

Column 39,
Line 6, "CMS" should read --CM5--.

In the Claims

Column 61,
Line 49, "CDR LE SEQ ID NO:2" should read --CDR L1, SEQ ID NO:2--.

Signed and Sealed this
Fifth Day of May, 2020

Andrei Iancu
*Director of the United States Patent and Trademark Office*